(12) United States Patent
Girotti et al.

(10) Patent No.: US 7,718,836 B2
(45) Date of Patent: May 18, 2010

(54) INTEGRATED PROCESS FOR THE PRODUCTION OF 2,6-DIMETHYLNAPHTHALENE

(75) Inventors: Gianni Girotti, Novara (IT); Giuseppe Terzoni, Piacenza (IT); Oscar Cappellazzo, Alghero (IT); Renzo Bignazzi, Legnano (IT); Giannino Pazzuconi, Broni (IT)

(73) Assignees: ENI S.p.A., Rome (IT); Polimeri Europa S.p.A., Brindisi (IT)

(*) Notice: Subject to any disclaimer, the term of this patent is extended or adjusted under 35 U.S.C. 154(b) by 542 days.

(21) Appl. No.: 10/162,607

(22) Filed: Jun. 6, 2002

(65) Prior Publication Data
US 2003/0069459 A1 Apr. 10, 2003

(30) Foreign Application Priority Data
Jun. 7, 2001 (IT) .......................... MI2001A1205

(51) Int. Cl.
*C07C 15/067* (2006.01)
(52) U.S. Cl. ................ 585/467; 585/320; 585/323; 585/448; 585/475
(58) Field of Classification Search ........... 585/448, 585/458, 467, 468, 323, 475, 320
See application file for complete search history.

(56) References Cited

U.S. PATENT DOCUMENTS

| 4,187,255 A | * | 2/1980 | Dodd ..................... 585/467 |
| 5,481,055 A | * | 1/1996 | Takagawa et al. ........... 585/481 |
| 5,744,670 A | * | 4/1998 | Motoyuki et al. ........... 585/320 |
| 6,018,086 A | * | 1/2000 | Motoyuki et al. ........... 585/323 |
| 6,018,087 A | * | 1/2000 | Motoyuki et al. ........... 585/481 |
| 6,057,487 A | * | 5/2000 | Munson et al. ............. 585/814 |
| 6,121,501 A | * | 9/2000 | Motoyuki et al. ........... 585/323 |
| 6,737,558 B2 | | 5/2004 | Bignazzi et al. |
| 2002/0023318 A1 | | 2/2002 | Bignazzi et al. |

FOREIGN PATENT DOCUMENTS

EP 1 069 102 1/2001

OTHER PUBLICATIONS

U.S. Appl. No. 11/333,201, filed Jan. 18, 2006, Pazzuconi, et al.

* cited by examiner

*Primary Examiner*—In Suk Bullock
(74) *Attorney, Agent, or Firm*—Oblon, Spivak, McClelland, Maier & Neustadt, L.L.P.

(57) ABSTRACT

The present invention relates to an integrated process for the production of high purity 2,6-dimethylnaphthalene starting from hydrocarbon mixtures containing naphthalene and/or isomers of methylnaphthalene and/or isomers of dimethylnaphthalene and/or isomers of polymethylnaphthalene, and from an alkylating agent, preferably methanol, reacted in the presence of a methylated benzene solvent or mixture of various methylated benzene solvents, preferably selected from toluene, xylene and trimethylbenzene, and a catalyst consisting of ZSM-12 zeolite and an inorganic ligand.

28 Claims, 5 Drawing Sheets

INTEGRATED PROCESS FOR THE PRODUCTION OF 2,6-DIMETHYLNAPHTHALENE

CROSS-REFERENCE TO RELATED APPLICATIONS

The present application claims priority to Italian application No. MI2001A 001205, filed on Jun. 7, 2001.

BACKGROUND OF THE INVENTION

Field of the Invention

The present invention relates to an integrated process for the production of high purity 2,6-dimethylnaphthalene starting from hydrocarbon mixtures containing naphthalene and/or isomers of methylnaphthalene and/or isomers of dimethylnaphthalene and/or isomers of polymethylnaphthalene, and from an alkylating agent, preferably methanol, reacted in the presence of a methylated benzene solvent or mixture of various methylated benzene solvents, preferably selected from toluene, xylene and trimethylbenzene, and a catalyst consisting of ZSM-12 zeolite and an inorganic ligand.

BRIEF DISCUSSION OF THE FIGS.

DETAILED DESCRIPTION OF THE PREFERRED EMBODIMENTS

Figure 1:
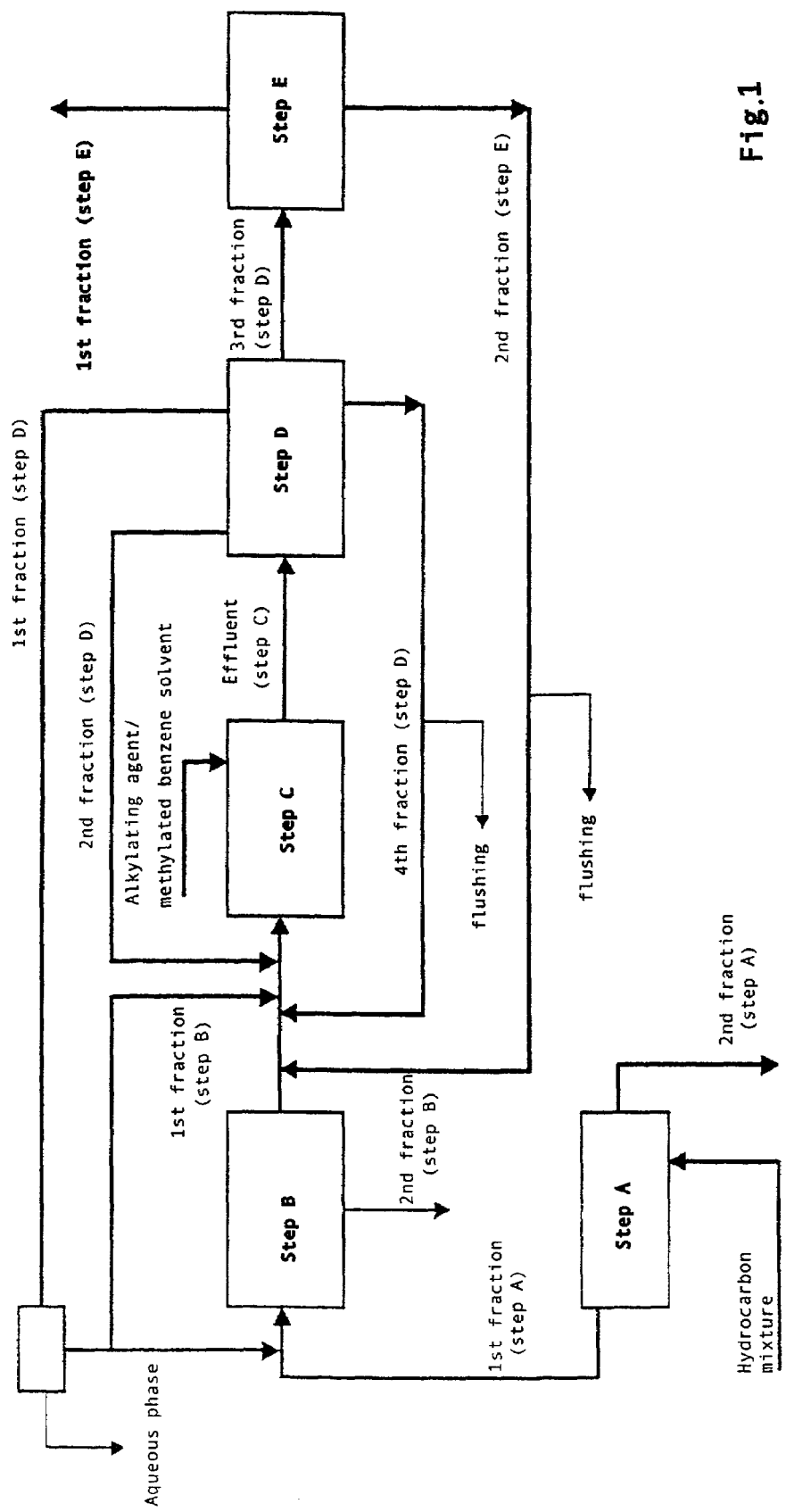
FIG. 1 shows a schematic representation of the first embodiment of the present invention.

Description of the First Embodiment of the Present Invention

More specifically, the present invention relates to a process for the preparation of high purity 2,6-dimethylnaphthalene starting from hydrocarbon mixtures containing naphthalene and/or isomers of methylnaphthalene and/or isomers of dimethylnaphthalene and/or isomers of polymethylnaphthalene, and from an alkylating agent which are reacted in a benzene solvent in the presence of a catalyst of a zeolitic nature, comprising the following steps:

A. Enrichment, by means of distillation, of the hydrocarbon mixture of interest with the consequent production of a first hydrocarbon fraction characterized by a high concentration of the above naphthalene compounds and a second fraction consisting of prevalently non-naphthalene compounds;

B. Treatment of the mixture of naphthalene compounds obtained in the previous step with an acid catalyst in a solvent medium of a benzene nature;

C. At least one chemical transformation of the mixture containing said solvent and said naphthalene compounds by reaction with an alkylating agent in a benzene solvent in the presence of a catalyst of a zeolitic nature;

D. Optionally, a second chemical transformation in the presence of a solvent different from the one used in the chemical transformation/s according to the previous step;

E. At least one separation phase, by distillation, of the mixtures resulting from the chemical transformations;

F. At least one purification phase of the mixtures coming from the chemical transformation phases, by means of crystallization operations and washings.

According to some preferred embodiments, the integrated process consists of the following steps:

A. Enrichment, by means of distillation, of a hydrocarbon mixture containing, among others, naphthalene and/or isomers of methylnaphthalene and/or isomers of dimethylnaphthalene and/or isomers of polymethylnaphthalene in order to obtain a first hydrocarbon fraction characterized by a higher concentration of said naphthalene compounds and a second fraction prevalently consisting of non-naphthalene compounds.

B. Purification of the hydrocarbon mixture obtained in the previous step A containing, among others, naphthalene and/or isomers of methylnaphthalene and/or isomers of dimethylnaphthalene and/or isomers of polymethylnaphthalene, by the reaction of said mixture with a solid acid catalyst in the presence of a methylated benzene solvent. The hydrocarbon mixture thus purified is then separated into a first fraction consisting of the benzene solvent and said naphthalene compounds and into a second hydrocarbon fraction prevalently containing heavy non-naphthalene compounds, initially present or formed in said purification step.

C. Chemical transformation of a hydrocarbon mixture containing, among others, naphthalene and/or isomers of methylnaphthalene and/or isomers of dimethylnaphthalene and/or isomers of polymethylnaphthalene, into a hydrocarbon mixture, said effluent from step C being enriched in the 2,6-dimethylnaphthalene isomer; the chemical transformation is carried out in the presence of an alkylating agent, preferably methanol, a methylated benzene solvent, preferably trimethylbenzene, or mixtures of various methylated benzene solvents starting from toluene up to hexamethylbenzene, and a solid acid catalyst consisting of ZSM-12 zeolite and an inorganic ligand.

D. Separation, by means of distillation, of a mixture containing an aqueous phase, various methylated benzene solvents, naphthalene and/or isomers of methylnaphthalene and/or isomers of dimethylnaphthalene and/or isomers of polymethylnaphthalene obtained from the previous step C and enriched in the 2,6 isomer in order to obtain a first fraction prevalently consisting of water and methylated benzene solvent, a second fraction consisting of the rest of the methylated benzene solvent, naphthalene and isomers of methylnaphthalene, a third fraction prevalently consisting of isomers of dimethylnaphthalene, including the 2,6 dimethylnaphthalene isomer and a fourth fraction prevalently consisting of polymethylnaphthalenes. The first fraction, after separation and removal of the aqueous phase, when present, by means of demixing, is partly re-fed to the previous step B and partly to the previous step C, the second fraction is re-fed to the previous step C, the third fraction is fed to the subsequent step E whereas the fourth fraction is re-fed, either totally or partially, to step C.

E. Purification of the third fraction obtained in step D and prevalently consisting of isomers of dimethylnaphthalene, by means of crystallization steps by cooling, subsequent washing and re-crystallizations carried out in the presence of a low molecular weight alcohol selected from methanol, ethanol and propanol, preferably methanol, to obtain a first fraction consisting of 2,6 dimethylnaphthalene with a very high degree of purity and a second fraction prevalently consisting of isomers of dimethylnaphthalene, comprising the 2,6 di-methylnaphthalene isomer. Said second fraction obtained in the present step E, prevalently consisting of isomers of dimethylnaphthalene, comprising the 2,6 dimethylnaphthalene isomer, is re-fed, either totally or partially, to the chemical transformation step C. The first fraction obtained in the present step E, consisting of 2,6 dimethylnaphthalene with a very high degree of purity, forms the end-product of the integrated process claimed herein.

The configuration described above is schematically represented in FIG. 1.

Description of the Second Embodiment of the Present Invention

The integrated process described herein can also be effected introducing new steps and/or modifications to the steps described above. In one of the particular aspects of the present invention, the integrated process is carried out as follows:

A. Enrichment, by means of distillation, of a hydrocarbon mixture containing, among others, naphthalene and/or isomers of methylnaphthalene and/or isomers of dimethylnaphthalene and/or isomers of polymethylnaphthalene in order to obtain a first hydrocarbon fraction characterized by a higher concentration of said naphthalene compounds and a second fraction prevalently consisting of non-naphthalene compounds.

B. Purification of the hydrocarbon mixture obtained in the previous step A containing, among others, naphthalene and/or isomers of methylnaphthalene and/or isomers of dimethylnaphthalene and/or isomers of polymethylnaphthalene, by the reaction of said mixture with a solid acid catalyst in the presence of a methylated benzene solvent. The hydrocarbon mixture thus purified is then separated into a first fraction consisting of the benzene solvent and said naphthalene compounds and into a second hydrocarbon fraction prevalently containing heavy non-naphthalene compounds, initially present or formed in said purification step.

C. Chemical transformation of a hydrocarbon mixture containing, among others, naphthalene and/or isomers of methylnaphthalene and/or isomers of dimethylnaphthalene and/or isomers of polymethylnaphthalene, into a hydrocarbon mixture, effluent from step C, enriched in the 2,6-dimethylnaphthalene isomer; said chemical transformation is carried out in the presence of an alkylating agent, preferably methanol, a methylated benzene solvent, or mixtures of various methylated benzene solvents, starting from toluene up to hexamethylbenzene, and a solid acid catalyst consisting of ZSM-12 zeolite and an inorganic ligand. The mixture of various methylated benzene solvents used in this step is such as to have an overall molar ratio between methyls and aromatic benzene ring equal to or higher than 2 and preferably equal to or higher than 3.

D. Separation, by means of distillation, of a mixture containing an aqueous phase, benzene and mixtures of various methylated benzene solvents, naphthalene and/or isomers of methylnaphthalene and/or isomers of dimethylnaphthalene and/or isomers of polymethylnaphthalene obtained from the previous step C and subsequent steps F and G, to obtain a first fraction prevalently consisting of water and benzene, toluene and xylenes and characterized by an overall molar ratio between methyls and benzene ring of less than 2, a second fraction prevalently consisting of tri-, tetra-, penta- and hexamethylbenzene and characterized by an overall molar ratio between methyls and benzene ring equal to or higher than 2 and preferably higher than 3, a third fraction prevalently consisting of naphthalene, a fourth fraction prevalently consisting of methylnaphthalene isomers, a fifth fraction prevalently consisting of isomers of dimethylnaphthalene comprising the 2,6 dimethylnaphthalene isomer and a sixth fraction prevalently consisting of polymethylnaphthalenes. The first fraction, after separation and removal of the aqueous phase, when present, by means of demixing, is partly sent to step B and partly to the subsequent step F, the second fraction is partly sent to step B and partly to the previous step C, the third fraction is partly sent to step F and partly to step C, the fourth fraction is sent to step C, the fifth fraction is sent to the subsequent step E and the sixth fraction is partly sent to step F and partly to step C.

E. Purification of the fifth fraction obtained in step D and prevalently consisting of isomers of dimethylnaphthalene, by means of crystallization steps by cooling, subsequent washing and re-crystallizations carried out in the presence of a low molecular weight alcohol selected from methanol, ethanol and propanol, preferably methanol, to obtain a first fraction consisting of 2,6 dimethylnaphthalene with a very high degree of purity and a second fraction prevalently consisting of isomers of dimethylnaphthalene, comprising the 2,6 dimethylnaphthalene isomer. Said second fraction obtained in the present step E, prevalently consisting of isomers of dimethylnaphthalene, comprising the 2,6 dimethylnaphthalene isomer, is partly sent to step C and partly to step F. The first fraction obtained in the present step E, consisting of 2,6 dimethylnaphthalene with a very high degree of purity, forms the end-product of the integrated process claimed herein.

F. Chemical transformation step of the hydrocarbon mixture containing, among others, naphthalene and/or isomers of dimethylnaphthalene and/or isomers of polymethylnaphthalene, carried out in the presence of a solid acid catalyst, preferably based on acid zeolites, and a mixture of various methylated benzene solvents prevalently consisting of benzene, toluene and xylenes and characterized by an overall molar ratio between methyls and benzene ring of less than 2, in order to obtain a hydrocarbon mixture characterized by a higher concentration of methylnaphthalene isomers and wherein said hydrocarbon mixture obtained in the present step F is partly sent to the previous separation step D by means of distillation and partly to the subsequent step G, again by means of separation by distillation.

G. Separation, by means of distillation, of a mixture containing benzene and mixtures of various methylated benzene solvents, naphthalene and/or isomers of methylnaphthalene and/or isomers of dimethylnaphthalene and/or isomers of polymethylnaphthalene obtained in the previous step F, to obtain a first fraction consisting of a mixture of various methylated benzene solvents, naphthalene and methylnaphthalene isomers and a second fraction prevalently consisting of dimethylnaphthalene isomers, including the 2,6 dimethylnaphthalene isomer, and polymethylnaphthalenes. The first fraction is sent to the separation by distillation step D whereas the second fraction is sent, either totally or partially, to the chemical transformation step F.

The configuration described above is schematically represented in FIG. 2.

Description of the Third Embodiment of the Present Invention

In another of the particular aspects of the present invention, the integrated process is carried out as follows:

A. Enrichment, by means of distillation, of a hydrocarbon mixture containing, among others, naphthalene and/or isomers of methylnaphthalene and/or isomers of dimethylnaphthalene and/or isomers of polymethylnaphthalene in order to obtain a first hydrocarbon fraction characterized by a higher concentration of said naphthalene compounds and a second fraction prevalently consisting of non-naphthalene compounds.

B. Purification of the hydrocarbon mixture obtained in the previous step A containing, among others, naphthalene and/or isomers of methylnaphthalene and/or isomers of dimethylnaphthalene and/or isomers of polymethylnaphthalene, by the reaction of said mixture with a solid acid catalyst in the presence of a methylated benzene solvent. The hydrocarbon mixture thus purified is then separated into a first fraction consisting of the benzene solvent and said naphthalene compounds and into a second hydrocarbon fraction prevalently containing heavy non-naphthalene compounds, initially present or formed in said purification step.

C. Chemical transformation of a hydrocarbon mixture containing among others, naphthalene and/or isomers of methylnaphthalene and/or isomers of dimethylnaphthalene and/or isomers of polymethylnaphthalene, into a hydrocarbon mixture, effluent from step C, enriched in the 2,6-dimethylnaphthalene isomer; said chemical transformation is carried out in the presence of an alkylating agent, preferably methanol, a methylated benzene solvent, or mixtures of various methylated benzene solvents, starting from toluene up to hexamethylbenzene, and a solid acid catalyst consisting of ZSM-12 zeolite and an inorganic ligand. The mixture of various methylated benzene solvents used in this step is such as to have an overall molar ratio between methyls and aromatic benzene ring equal to or higher than 2 and preferably equal to or higher than 3.

D. Separation, by means of distillation, of a mixture containing an aqueous phase, benzene and mixtures of various methylated benzene solvents, naphthalene and/or isomers of methylnaphthalene and/or isomers of dimethylnaphthalene and/or isomers of polymethylnaphthalene obtained from the previous step C and subsequent steps F and G, to obtain a first fraction prevalently consisting of water and benzene, toluene and xylenes and characterized by an overall molar ratio between methyls and benzene ring of less than 2, a second fraction prevalently consisting of tri-, tetra-, penta- and hexamethylbenzene and characterized by an overall molar ratio between methyls and benzene ring equal to or higher than 2 and preferably higher than 3, a third fraction prevalently consisting of naphthalene, a fourth fraction prevalently consisting of methylnaphthalene isomers, a fifth fraction prevalently consisting of isomers of dimethylnaphthalene comprising the 2,6 dimethylnaphthalene isomer and a sixth fraction prevalently consisting of polymethylnaphthalenes. The first fraction, after separation and removal of the aqueous phase, when present, by means of demixing, is partly sent to step B and partly to the subsequent step F, the second fraction is partly sent to step B and partly to the previous step C, the third fraction is partly sent to step F and partly to step C, the fourth fraction is sent to step C, the fifth fraction is sent to the subsequent step H and the sixth fraction is partly sent to step F and partly to step C E. Purification of the first fraction obtained in step H and prevalently consisting of isomers of dimethylnaphthalene characterized by a high concentration of the 2,6 isomer and a low concentration of the 1,6 and 1,5 dimethylnaphthalene isomers, by means of crystallization steps by cooling, subsequent washing and recrystallizations carried out in the presence of a low molecular weight alcohol selected from methanol, ethanol and propanol, preferably methanol, to obtain a first fraction consisting of 2,6 dimethylnaphthalene with a very high degree of purity and a second fraction prevalently consisting of isomers of dimethylnaphthalene, comprising the 2,6 dimethylnaphthalene isomer. Said second fraction obtained in the present step E, prevalently consisting of isomers of dimethylnaphthalene, comprising the 2,6 dimethylnaphthalene isomer, is partly sent to step C and partly to step F. The first fraction obtained in the present step E, consisting of 2,6 dimethylnaphthalene with a very high degree of purity, forms the end-product of the integrated process claimed herein.

F. Chemical transformation step of the hydrocarbon mixture containing, among others, naphthalene and/or isomers of dimethylnaphthalene and/or isomers of polymethylnaphthalene, carried out in the presence of a solid acid catalyst, preferably based on acid zeolites, and a mixture of various methylated benzene solvents prevalently consisting of benzene, toluene and xylenes and characterized by an overall molar ratio between methyls and benzene ring of less than 2, in order to obtain a hydrocarbon mixture characterized by a higher concentration of methylnaphthalene isomers and wherein said hydrocarbon mixture obtained in the present step F is sent to the subsequent separation by distillation step G.

G. Separation, by means of distillation, of a mixture containing benzene and mixtures of various methylated benzene solvents, naphthalene and/or isomers of methylnaphthalene and/or isomers of dimethylnaphthalene and/or isomers of polymethylnaphthalene obtained in the previous step F, to obtain a first fraction consisting of a mixture of various methylated benzene solvents, naphthalene and methylnaphthalene isomers and a second fraction prevalently consisting of dimethylnaphthalene isomers, including the 2,6 dimethylnaphthalene isomer, and polymethylnaphthalenes. The first fraction is sent to the separation by distillation step D whereas the second fraction is sent, either totally or partially, to the chemical transformation step F.

H. Separation, by means of distillation, of a hydrocarbon mixture prevalently consisting of dimethylnaphthalene isomers in order to obtain a first fraction prevalently consisting of dimethylnaphthalene isomers with a higher concentration of the 2,6 isomer and a lower concentration of 1,6 and 1,5 dimethylnaphthalene isomers, with respect to the initial concentrations of the mixture fed to the present step, and a second fraction prevalently consisting of dimethylnaphthalene isomers with a lower concentration of the 2,6 isomer and higher concentration of 1,6 and 1,5 dimethylnaphthalene isomers, with respect to the initial concentrations of the mixture fed to the present step. The first fraction obtained in the present step H is sent to the previous step E whereas the second fraction is sent to the subsequent chemical transformation step I.

I. Chemical transformation step of the hydrocarbon mixture consisting of the second fraction obtained in the previous step H and prevalently containing dimethylnaphthalene isomers in order to obtain a hydrocarbon mixture characterized by a higher concentration of 2,6 dimethylnaphthalene isomer, with respect to the initial concentration of the mixture fed to the present step. Said chemical transformation step I is carried out in the presence of a solid acid catalyst and preferably in the presence of a catalyst analogous to that used in the previous chemical transformation step C. The hydrocarbon mixture obtained in the present chemical transformation step I is sent, either totally or partially, to the separation by distillation step H.

The configuration described above is schematically represented in FIG. 3.

SUMMARY OF THE INVENTION

The various steps which form the integrated process claimed herein are carried out under certain conditions relating to the flow-rate of the reagents, relative ratios between these, temperatures, pressures and other aspects characterizing each step which are described hereunder.

Step A, in which the hydrocarbon mixture containing, among others, naphthalene and/or isomers of methylnaphthalene and/or isomers of dimethylnaphthalene and/or isomers of polymethylnaphthalene, is fed, is carried out using conventional distillation methods in order to obtain a hydrocarbon mixture characterized by a concentration of not less than 20% of naphthalene compounds.

Step B, in which the hydrocarbon mixture obtained in the previous step A and containing, among others, naphthalene and/or isomers of methylnaphthalene and/or isomers of dimethylnaphthalene and/or isomers of polymethylnaphthalene, is fed, is carried out according to the procedure already described in IT MI 99/A 1533 and in particular in the presence of a benzene solvent, preferably selected from toluene, xylene and trimethylbenzene, and a solid acid catalyst selected from clays (montmorillonites, smectites, etc.), acid or partially acid zeolites, sulfated zirconia, acid resins (e.g. sulfonic resins), aluminas, activated aluminas, chlorinated or fluorinated aluminas, amorphous silico-aluminas, acid oxides in general, heteropolyacids, partially salified heteropolyacids (with Cs or other metals) or supported acids (e.g. phosphoric acid on silica or other natural and synthetic carriers).

The separation of the reaction effluent effected in step B into a first fraction consisting of the benzene solvent and naphthalene compounds and into a second fraction containing heavy non-naphthalene compounds, is carried out 10 using conventional distillation methods.

Step B is carried out in continuous, semi-continuous or batchwise, at a temperature ranging from room temperature to 360° C. and at a pressure which is such as to maintain the system in completely liquid phase. If the operation is carried out batchwise or in semi-continuous, the quantity of solid acid catalyst to be used ranges from 0.1% to 5% of the overall hydrocarbon mixture to be treated coming from step A, for a treatment time not exceeding 5 minutes. If the operation is carried out in continuous, the hydrocarbon mixture coming from step A is fed to step B with a WHSV ranging from 0.1 $h^{-1}$ to 6 $h^{-1}$.

Step C in which the chemical transformation is effected of the hydrocarbon mixture containing, among others, naphthalene and/or isomers of methylnaphthalene and/or isomers of dimethylnaphthalene and/or isomers of polymethylnaphthalene, is carried out in the presence of a benzene solvent or mixtures of various methylated benzene solvents, preferably trimethylbenzene, a methylating agent, preferably methanol and a solid acid catalyst consisting of ZSM-12 zeolite and an inorganic ligand. The catalyst is in the form of cylindrical pellets, spheres or other forms commonly used, but preferably in pellets, whereas the inorganic ligand of which it is formed, is selected from aluminas, silicas, silico-aluminas, titania, zirconia or clays but preferably alumina. In the end-catalyst, consisting of ZSM-12 zeolite and an inorganic ligand, the weight ratio between zeolite and inorganic ligand ranges from 10:90 to 90:10, but preferably from 25:75 to 75:25.

In its preferred form, the end-catalyst is also characterized by particular extra-zeolitic porosity properties, i.e. the porosity fraction of the catalyst not attributable to the quality and quantity of zeolite present in the end-catalyst. In particular, this extra-zeolitic porosity has values of not less than 0.4 ml/g of end-catalyst associated with a fraction equal to at least 50% of said extra-zeolitic porosity characterized by pores having a diameter of over 100 Å. Said extra-zeolitic porosity is correctly determined according to known methods described for example in "Introduction to powder surface area" Loweel, Seymour-Wiley Interscience publ.

The ZSM-12 zeolite forming the end-catalyst is characterized by an aluminum content present in the zeolite, expressed as $[SiO_2]/[Al_2O_3]$, greater than or equal to 20 and in that it is in at least partially acid form, i.e. in a form in which at least 50% of the cationic sites present in the ZSM-12 zeolite is occupied by hydrogen ions (acid sites) and even more preferably at least 90% of said cationic sites is occupied by hydrogen ions.

The molar ratio between benzene solvent and the total moles of naphthalene compounds contained in the hydrocarbon mixture used in this step C ranges from 1 to 100 and preferably from 3 to 20.

The molar ratio between the methylating agent and total moles of naphthalene compounds contained in the hydrocarbon mixture used in this step is lower than 30 and preferably ranges from 0.1 to 3.

The temperature at which step C is carried out ranges from 200° C. to 450° C. and preferably from 250 to 350° C.

The overall flow-rate of the reagents fed to step C, expressed as WHSV, ranges from 0.01 $h^{-1}$ to 8 $h^{-1}$ and preferably from 0.1 $h^{-1}$ to 4 $h^{-1}$.

The pressure at which step C is carried out is selected at such values as to guarantee that the chemical transformation takes place in at least partially liquid phase and preferably in completely liquid phase.

Step C can be carried out in continuous, batchwise or in semi-continuous; the catalyst can be arranged in one or more fixed catalytic beds and a fraction of the total quantity of hydrocarbon mixture and/or a fraction of the total quantity of benzene solvent used and/or a fraction of the total quantity of alkylating agent used and/or a quantity of inert substance, can be fed between one bed and another, in order to improve the selectivity of step C, or cooling can be effected between one layer of the catalyst and the subsequent one, using a refrigerant.

Step D, in which the separation takes place of the various naphthalene fractions and benzene solvent used together with the separation of the aqueous phase present from the organic phase, is carried out using conventional distillation methods and demixing by cooling.

Step E relating to the separation of the 2,6 dimethylnaphthalene isomer starting from the fraction prevalently consisting of dimethylnaphthalene obtained in the previous steps D or H, is carried out by means of a crystallization step $E_a$ by cooling and subsequent separation of the solid obtained, a step $E_b$ which comprises one or more washing phases and subsequent separation of the solid obtained and a step $E_c$ which comprises a re-dissolution phase of the precipitate obtained in step $E_b$, a re-crystallization phase of the mixture thus obtained and subsequent separation of the solid obtained, said steps $E_a$, $E_b$ and $E_c$ being carried out in the presence of a low molecular weight alcohol selected from methanol, ethanol, propanol and glycols, preferably methanol.

The quantity of low molecular weight alcohol used in the crystallization phase $E_a$ by cooling in slurry under static conditions and/or under stirring or scored surface crystallization, ranges from 0.001 to 10 times by weight the total quantity of hydrocarbon mixture prevalently consisting of dimethylnaphthalene isomers to be crystallized and preferably said quantity of low molecular weight alcohol ranges from 0.1 to 10 times the quantity of hydrocarbon mixture to be crystallized. The washing phase $E_b$ of the precipitate thus obtained is carried out by re-dispersion of the solid, obtained by crystallization after separation from the remaining mother liquor liquid phase, in a low molecular weight alcohol and subsequent separation of the solid until a residual content of mother liquor of the previous crystallization of not over 30% by weight is obtained with respect to the total quantity of solid plus the wetting mother liquor and preferably not over 10% by weight of said quantity.

The recrystallization phase $E_c$ of the precipitate obtained from the previous washing phase is carried out in the presence of a low molecular weight alcohol, preferably selected from methanol, ethanol, propanol and glycols, more preferably methanol, using a quantity of said alcohol at least equal to the minimum quantity necessary for the dissolution of said precipitate at a temperature ranging from room temperature to 120° C. and more preferably at a temperature ranging from 50 to 120° C. and subsequently proceeding with the recrystallization by cooling the solution thus obtained and/or by evaporating the alcohol solvent used, under static conditions or under stirring. Said recrystallization phase can also be carried out using a quantity of alcohol solvent lower than the minimum quantity necessary for dissolving the precipitate obtained from the previous washing phase, preferably using a quantity of alcohol ranging from 20% to 80% of said minimum quantity, operating at a temperature ranging from room temperature to 120° C. and more preferably at a temperature ranging from 50 to 120° C., keeping the system under stirring for a certain period of time, and subsequently proceeding with the recrystallization phase starting from an alcohol mixture in which part of the starting precipitate obtained from the previous washings is therefore still present.

The recrystallization phase in which the quantity of alcohol solvent used is less than the minimum quantity necessary for the complete dissolution of the precipitate, can also be carried out by subjecting the alcohol dispersion containing part of the precipitate to one or more cooling and heating cycles before proceeding with the recrystallization according to what is described above.

The precipitate obtained from the recrystallization phase is separated from the liquid phase, prevalently consisting of the low molecular weight alcohol used, by means of conventional decanting, centrifugation, filtration and final evaporation methods, optionally under vacuum to eliminate the residual solvent, in order to obtain the 2,6 dimethylnaphthalene isomer with a very high degree of purity, at least with a purity of 2,6 dimethylnaphthalene of not less than 99%.

In order to illustrate the various possible operating configurations of step E, comprising steps $E_a$, $E_b$ and $E_c$ described above, two possible process schemes relating to step E alone of the integrated process claimed herein, with a quantified balance, are shown in the figures relating to examples 6 and 7.

In particular, the figure relating to example 6 shows a process scheme which does not comprise any recycling and re-use in the various steps $E_a$, $E_b$ and $E_c$ of the alcohol solvent used as also of the mother liquor produced in said steps.

The figure relating to example 7, on the other hand, shows a process scheme which includes complete recycling within step E of the alcohol solvent used and also of the mother liquor produced in steps $E_a$, $E_b$ and $E_c$.

The chemical transformation step F is carried out at a temperature ranging from 200° C. to 450° C. and preferably ranging from 250° C. to 350° C., in the presence of a solid acid catalyst, preferably in the presence of a catalyst consisting of acid zeolites of the large pore group, preferably Y zeolites, Beta zeolites and ZSM-12 and an inorganic ligand analogous to that already used in the chemical transformation step C, with a WHSV of the total reagents fed to said step F ranging from $0.1\ h^{-1}$ to $10\ h^{-1}$ whereas the pressure is selected so that the chemical transformation takes place in at least partially liquid phase, preferably at such a pressure as to guarantee that the chemical transformation takes place in the presence of a completely liquid phase.

Step G, in which the various naphthalene fractions and benzene solvent used, are separated, is carried out by means of conventional condensation by cooling and distillation methods.

Step H, in which the hydrocarbon mixture, prevalently consisting of dimethylnaphthalene isomers, is separated by distillation in order to obtain a fraction enriched in the 2,6 dimethylnaphthalene isomer and a fraction with a low concentration of this isomer, is carried out using conventional distillation methods.

The chemical transformation step I is carried out at a temperature ranging from 150° C. to 400° C. and preferably ranging from 200° C. to 350° C., in the presence of a solid acid catalyst, preferably in the presence of a catalyst consisting of acid zeolites of the large pore group, preferably Y zeolites, Beta zeolites and ZSM-12 and more preferably ZSM-12 zeolite and an inorganic ligand analogous to that already used in the chemical transformation step C, with a WHSV of the total reagents fed in said step I ranging from $0.01\ h^{-1}$ to $20\ h^{-1}$ and preferably from $4\ h^{-1}$ to $16\ h^{-1}$, whereas the pressure is selected so that the chemical transformation takes place in at least partially liquid phase, preferably at such a pressure as to guarantee that the chemical transformation takes place in the presence of a completely liquid phase.

DESCRIPTION OF THE STATE OF THE ART

The 2,6 dimethylnaphthalene isomer is used as precursor of 2,6 naphthalenedicarboxylic acid or the corresponding dimethyl ester, used in turn in the production of polyethylenenaphthalate polyester, obtained by condensation with ethylene glycol.

There are numerous applications of PEN, which mainly comprise the production of recyclable food bottles, high quality video tapes, advanced photographic applications and components for tyre manufacturing.

The particular and special properties of PEN end-products mainly consist in their high mechanical resistance, high thermal resistance and excellent gas barrier properties (oxygen and carbon dioxide). PEN applications are currently limited due to the poor availability and high cost of 2,6 dimethylnaphthalene which is produced according to an onerous process from an economic point of view, characterized by numerous passages, as described for example in U.S. Pat. No. 4,990,717 and U.S. Pat. No. 5,073,670.

U.S. Pat. No. 4,990,717 describes a process for the preparation of 2,6 dimethylnaphthalene starting from o-xylene and butadiene characterized by numerous reaction passages.

The first step comprises the preparation of 5-(o-tolyl)-pentene-2 by means of the alkenylation of o-xylene with butadiene in the presence of a catalyst. The second step involves the preparation of 1,5 dimethyltetraline by the cyclization of 5-(o-tolyl)-pentene-2 in the presence of a catalyst. The third step includes the preparation of 1,5 dimethylnaphthalene by means of the dehydrogenation of 1,5 dimethyltetraline in the presence of a catalyst. The fourth step comprises the preparation of a mixture of dimethylnaphthalenes enriched in the 2,6 dimethylnaphthalene isomer by means of the isomerization of 1,5 dimethylnaphthalene in the presence of a catalyst. The process then comprises all the necessary purification steps, including that for the production of the 2,6 dimethylnaphthalene isomer.

This process consequently has numerous disadvantages among which a high cost of the raw materials, extremely high investment costs and also very high production costs.

U.S. Pat. No. 5,001,295 describes a process for the preparation of 2,6 dimethylnaphthalene by means of alkylation starting from 2-methylnaphthalene and naphthalene in the presence of a synthetic zeolite of the MCM-22 type; U.S. Pat. No. 4,795,847 proposes a similar process which uses naphthalene and 2-methylnaphthalene in the presence of an alkylating agent and a synthetic zeolite of the ZSM-5 type.

The poor availability on an industrial scale of 2-methylnaphthalene, intrinsic limitations relating to the destination of the dimethylnaphthalene fraction produced and low productivity are negative characteristics which do not allow the commercial acceptance of the processes claimed.

U.S. Pat. No. 6,011,190 describes a process for the preparation of 2,6 dimethylnaphthalene starting from naphthaline in the presence of an alkylating agent and a synthetic zeolite of the MCM-22 type in which the dimethylnaphthalene fraction obtained in the alkylation step of naphthaline is separated from the reaction effluent and reacted with naphthaline, in the presence of the same catalyst, to enrich, by isomerization, the 2,6 dimethylnaphthalene fraction present and at the same time enrich, by transalkylation, the methylnaphthalene fraction, which are then re-fed to the alkylation step carried out in the presence of the alkylating agent. The process is completed by various separation steps of the different groups of components formed during the reaction steps and in particular, a high pressure crystallization process is described for obtaining the 2,6 dimethylnaphthalene isomer starting from the mixture containing the various dimethylnaphthaline isomers.

The economic convenience of the process described in terms of productivity and operating costs depends on the ratio between the 2,6 dimethylnaphthalene isomer and total dimethylnaphthalenes and the ratio between the 2,6 dimethylnaphthalene isomer and 2,7 dimethylnaphthalene isomer which the various chemical transformation steps in the presence of a catalyst are able to guarantee, as well as the effectiveness of the specific crystallization step for obtaining 2,6 dimethylnaphthalene with a sufficient degree of purity for subsequent uses.

The higher the 2,6 dimethylnaphthalene fraction with respect to the total dimethylnaphthalenes in the various chemical transformation steps, with the same efficiency of the crystallization step, the higher the specific productivity will be, with a considerable benefit from the point of view of operating and running costs. A high 2,6 dimethylnaphthalene fraction with respect to the total dimethylnaphthalenes does in fact indicate an extremely selective catalytic system, considering that the transformation of the various dimethylnaphthalene isomers in the 2,6 dimethylnaphthalene is only relatively easy for some of these and intrinsically very difficult for others.

It should be noted however that the separation of the 2,6 dimethylnaphthalene isomer from the remaining dimethylnaphthalene isomers and in particular the 2,7 dimethylnaphthalene isomer is also extremely difficult.

The difference in the boiling points between the 2,6 dimethylnaphthalene isomer and 2,7 dimethylnaphthalene isomer is in fact only 0.3° C., whereas separation by crystallization, to which resort must be made, causes the formation of very fine crystals of the 2,6 dimethylnaphthalene isomer, which remain in suspension in the mother liquor making its recovery difficult.

Furthermore, 2,6 and 2,7 isomers form a eutectic mixture when their ratio in the crystallization mother liquor reaches a value of 0.7 and consequently a low productivity of the crystallization step and therefore a low specific productivity of the whole process corresponds to low 2,6/2,7 ratio values in the mixture of dimethylnaphthalenes from which the 2,6 dimethylnaphthalene isomer is to be obtained In the various examples provided in U.S. Pat. No. 6,011, 190, a percentage ratio of 2,6 dimethylnaphthalene/total dimethylnaphthalenes varying from 10.02% (Ex. 9, column 14) to 17.4% (Ex. 7, column 13) is obtained, with a 2,6/2,7 ratio varying from 1.61 to 1.36 and with a purity of 2,6 dimethylnaphthalene produced in the high pressure crystallization step equal to 87%.

DISCUSSION OF THE PRESENT INVENTION RELATIVE TO THE STATE OF THE ART

In the integrated process claimed herein, which is more clearly described in the following examples provided for illustrating said process without limiting or favouring any of its aspects, much better results are obtained which enable the integrated process claimed herein to be effectively applied from an industrial point of view for a wide-scale production of 2,6 dimethylnaphthalene, with high specific productivities and low operating costs.

The process claimed herein allows chemical transformations to be obtained in the reaction steps, characterized by the production of dimethylnaphthalene mixtures with 2,6 dimethylnaphthalene/total dimethylnaphthalene ratios >30% together with a 2,6 dimethylnaphthalene/2,7 dimethylnaphthalene ratio still higher than the value corresponding to the thermodynamic equilibrium between the two isomers, which is extremely important for the effectiveness of the separation step of the pure 2,6 dimethylnaphthalene isomer as also for the specific productivity of the whole process.

These results are due to the specific nature of the catalyst system/solvent used in the reaction step which form the integrated process for the production of 2,6 dimethylnaphthalene claimed herein.

In the process claimed herein, in fact, extremely high purities of 2,6 dimethylnaphthalene are obtained, higher than 99w, due to the synergy between the innovative crystallization process claimed herein and the high selectivity of the chemical transformation steps in which 2,6 dimethylnaphthalene is synthesized.

In particular, we would like to point out how the integrated process claimed herein consists, in one of the preferred aspects, of a single reaction step in which all the alkylation, transalkylation and isomerization steps necessary for the selective formation of 2,6 dimethylnaphthalene are effected.

These reactions, in other processes already described above, are, on the contrary, effected in separate steps with a considerable increase in the investment costs for an industrial application as well as in the operating costs of the industrial plant itself.

Another preferred aspect for the embodiment of the integrated process claimed herein comprises, on the other hand, a reaction section which is made up of two reactors, one of which dedicated to the alkylation of hydrocarbon mixtures prevalently consisting of isomers of monomethylnaphthalene and the other dedicated to the transalkylation and isomerization of hydrocarbon mixtures prevalently consisting of dimethylnaphthalenes and polymethylnaphthalenes. Also in this case, the process is characterized by all the positive aspects described above and, in addition, allows streams with varying compositions (streams characterized by high concentrations of polymethylated naphthalenes such as those deriving from LCO) to be used and exploited without the necessity of repeated flushings of the process streams which would be required for maintaining and guaranteeing high yields with respect to the reagents.

Another characteristic of the integrated process claimed herein is the high efficiency of the separation step of pure 2,6 dimethylnaphthalene starting from the hydrocarbon mixture prevalently consisting of dimethylnaphthalenes, together with low investment and operating costs of said separation step compared for example with the separation step by high pressure crystallization described in U.S. Pat. No. 6,011,190 and, in more detail, in U.S. Pat. No. 6,018,087.

U.S. Pat. No. 6,018,087 in fact, describes a process for the preparation of 2,6 dimethylnaphthalene starting from hydrocarbon mixtures containing dimethylnaphthalene isomers by means of the isomerization of said mixtures in the presence of a synthetic zeolite of the MCM-22 type and subsequent high pressure crystallization step of the hydrocarbon mixture obtained from the previous isomerization step.

Figure 2:
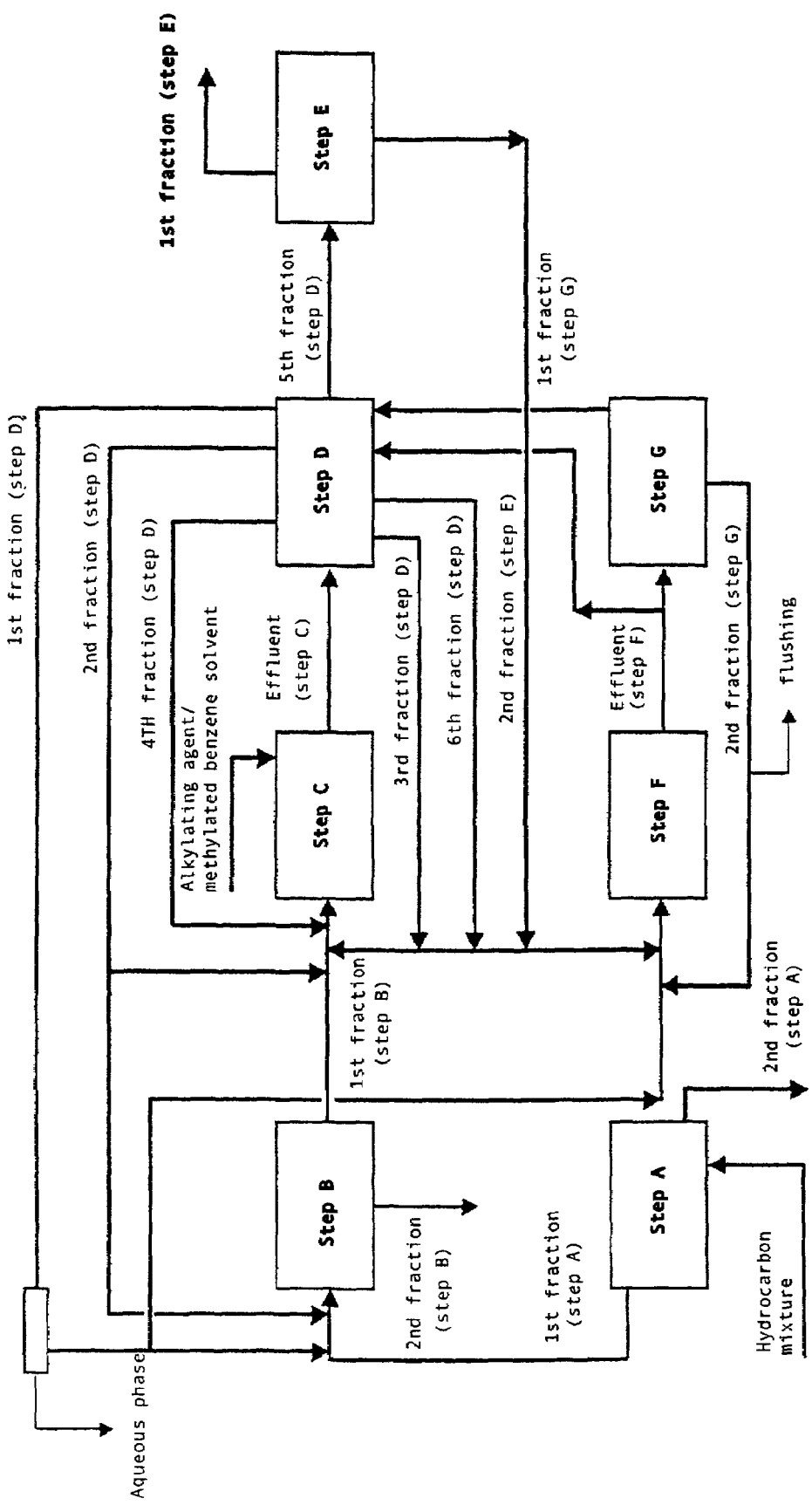
FIG. 2 shows a schematic representation of the second embodiment of the present invention.
Figure 3:
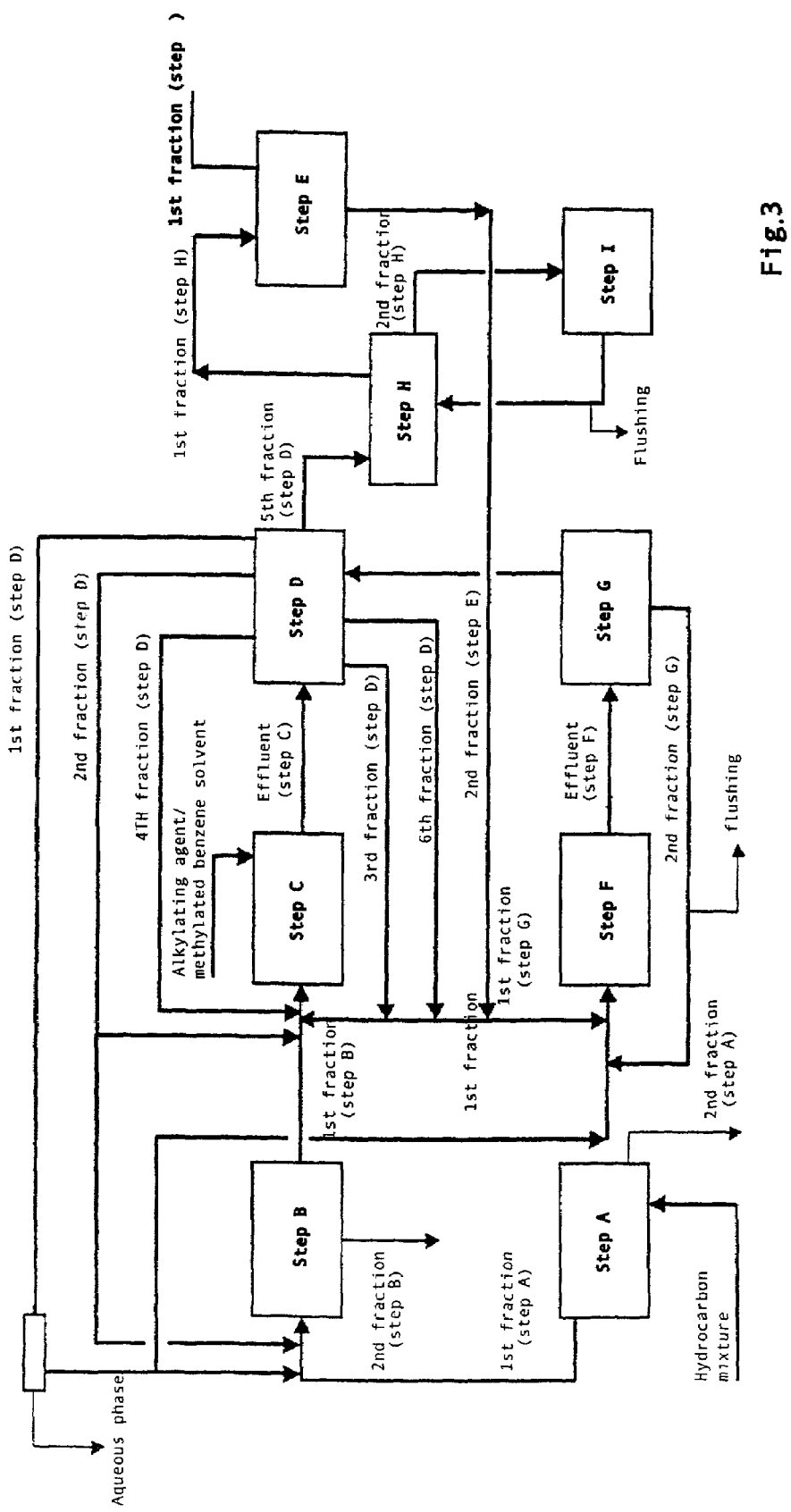
FIG. 3 shows a schematic representation of the third embodiment of the present invention.
Figure 4:
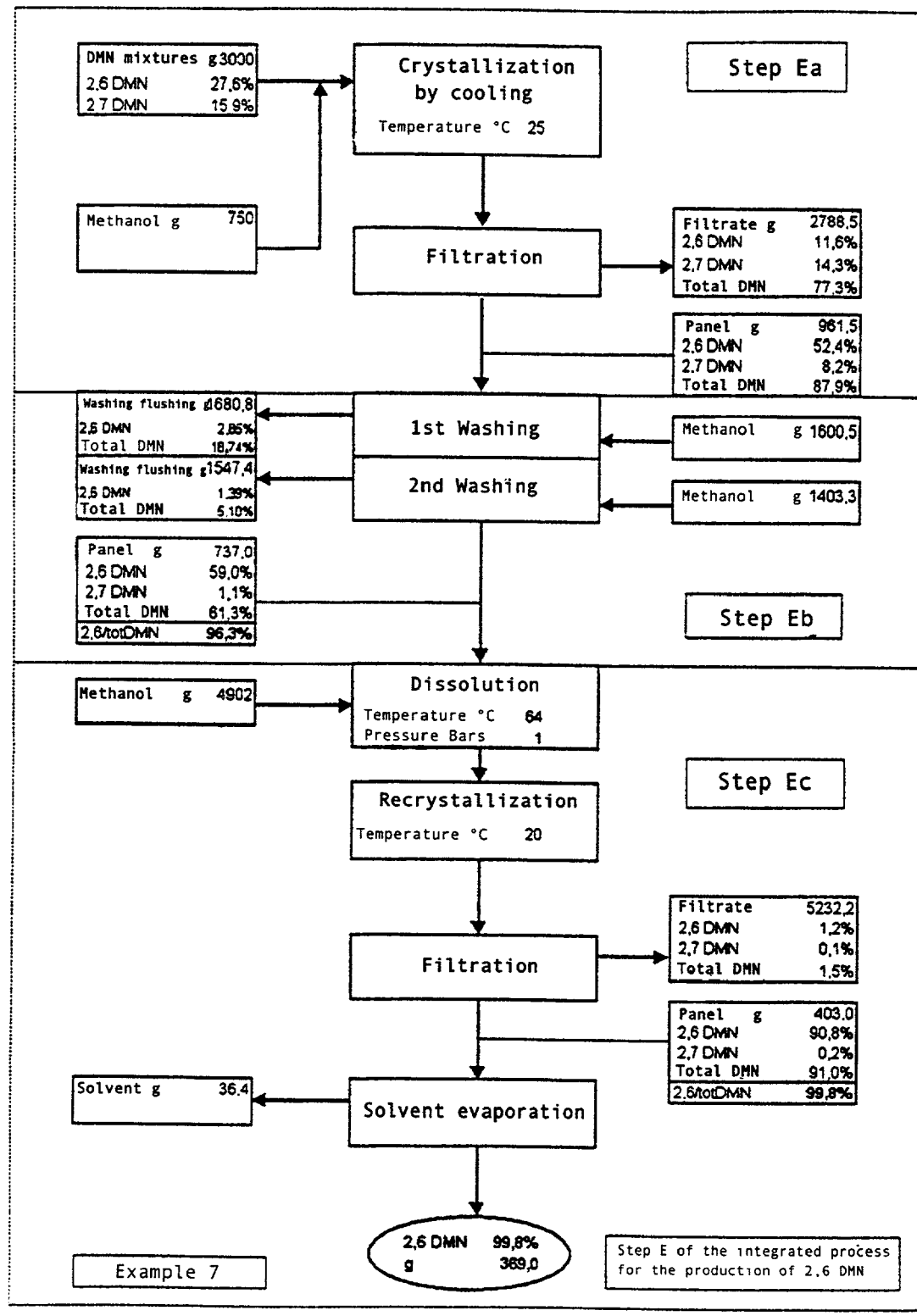
FIG. 4 shows the extraction and purification of 2,6-dimethylnaphthalene described in Example 7.

The crystallization step described is carried out at extremely high pressures, ranging from 900 kgf/cm$^2$ to 1500 kgf/cm$^2$, and it can be deduced, from observing the schemes indicated in FIGS. 2 to 4, that very low yields of the crystallization step are associated with high purities of 2,6 dimethylnaphthalene and viceversa.

This, in fact, is due to the composition of the hydrocarbon mixture containing dimethylnaphthalene isomers which is fed to the separation step by crystallization, characterized by low 2,6 dimethylnaphthalene/total dimethylnaphthalene ratios and low 2,6 dimethylnaphthalene/2,7 dimethylnaphthalene ratios.

One of the particular characteristics of the process claimed herein is therefore a high selectivity of the chemical transformation step(s), in which high values are reached of the 2,6 dimethylnaphthalene/total dimethylnaphthalene ratio together with high values of the 2,6 dimethylnaphthalene/2,7 dimethylnaphthalene ratio, combined with a high efficiency of the separation step by crystallization.

The high selectivity of the chemical transformation step can, in fact, be attributed to the innovative catalytic system used, associated with the benzene solvent, in particular trimethylbenzene, whereas the high performances of the crystallization step can be attributed to the innovative system adopted which involves the use of a particular solvent, preferably methanol.

Another particularly innovative aspect of the integrated process claimed herein consists of the considerable duration of the catalyst used and consequent stability of the catalytic performances, in terms of selectivity and yields, already discussed above.

This result has been obtained by means of the various innovative aspects which characterize the integrated process claimed herein.

The concentration step A and purification step B of the hydrocarbon mixture containing, among others, naphthalene and/or methylnaphthalene and/or dimethylnaphthalene and/or trimethylnaphthalene guarantee, in fact, a stream which is particularly suitable for the subsequent chemical transformation steps C, F and I.

The catalyst used in the integrated process claimed herein, in particular in step C and I, is another of the elements which contribute to the high duration and stability in the catalytic performances specified above.

The type and quality of zeolite contained in the end-catalyst together with the particular properties in terms of quantity and quality of the extra-zeolitic porosity described above form the specific characteristics of the catalytic system used in the integrated process described herein for the production of 2,6 dimethylnaphthalene.

EXAMPLES

Example 1

Separation by Means of Distillation and Subsequent Pre-treatment of Hydrocarbon Mixtures Prevalently Consisting of Naphthalene and/or Isomers of Methylnaphthalene and/or Isomers of Dimethylnaphthalene. (Step A and Step B)

The following example describes, for purely illustrative purposes, the distillation (step A) and pretreatment (step B) steps included in the integrated process, object of the present invention without limiting its scope in any way.

A sample of FOK from steam cracking of virgin naphtha characterized by the following w/w percentage composition: 10.2% of non-naphthalene light hydrocarbons with b.p. up to 205° C., 29.8% of naphthalene and methylnaphthalenes, 3.2% of naphthalene and non-naphthalene hydrocarbons with b.p. ranging from 212 to 226° C., 6.6% of naphthalene and non-naphthalene hydrocarbons with b.p. ranging from 246 to 260° C., 7.4% of dimethylnaphthalenes, 42.8% of naphthalene and non-naphthalene hydrocarbons with b.p. ranging from 270° C. upwards, is distilled in an experimental laboratory apparatus equipped with several distillation columns under such conditions as to obtain a distilled fraction characterized by the following w/w percentage composition: 0.9% of non-naphthalene light hydrocarbons with b.p. up to 205° C., 85.0% of naphthalene and methylnaphthalenes, 10.1% of naphthalene and non-naphthalene hydrocarbons with b.p. ranging from 212 to 226° C., 3.4% of naphthalene and non-naphthalene hydrocarbons with b.p. ranging from 246 to 260° C., 0.6% of dimethylnaphthalenes and less than 0.1% of naphthalene and non-naphthalene hydrocarbons with b.p. ranging from 270° C. upwards.

The distillate is then diluted in trimethylbenzene in such a quantity as to have a molar ratio between trimethylbenzene and the sum of naphthalene, methylnaphthalene and dimethylnaphthalene moles equal to 10.

The mixture thus obtained is reacted in a closed laboratory flask, under stirring, in the presence of an acid clay of the montmorillonite type in a quantity equal to 3% by weight with respect to the total quantity of mixture reacted, at a temperature of 80° C. for a time equal to 5 hours.

At the end of the reaction, the liquid product discharged from the reactor had the following w/w percentage composition (excluding the fraction of trimethylbenzene solvent): 1.3% of non-naphthalene light hydrocarbons with b.p. up to 205° C., 81.6% of naphthalene and methylnaphthalenes 6.0% of naphthalene and non-naphthalene hydrocarbons with b.p. ranging from 212 to 226° C., 0.3% of naphthalene and non-naphthalene hydrocarbons with b.p. ranging from 246 to 260° C., 0.5% of dimethylnaphthalenes and 10.4% of naphthalene and non-naphthalene hydrocarbons with b.p. ranging from 270° C. upwards. The hydrocarbon mixture thus obtained is distilled in an experimental laboratory apparatus equipped with several distillation columns under such conditions as to obtain a first fraction consisting of methylated benzene solvent and naphthalene and non-naphthalene compounds and a second fraction containing heavy non-naphthalene compounds, initially present or formed during said purification step. The first fraction had the following w/w percentage composition (excluding the fraction of methylated benzene solvent): 1.4% of non-naphthalene light hydrocarbons with b.p. up to 205° C., 91.0% of naphthalene and methylnaphthalenes, 6.6% of naphthalene and non-naphthalene hydrocarbons with b.p. ranging from 212 to 226° C., 0.3% of naphthalene and non-naphthalene hydrocarbons with b.p. ranging from 246 to 260° C., 0.5% of dimethylnaphthalenes and 0.1% of naphthalene and non-naphthalene hydrocarbons with b.p. ranging from 270° C. upwards.

Detailed gaschromatographic analysis on the first fraction obtained from the latter distillation showed a significant reduction in the non-naphthalene components present in the starting mixture and in particular of those present to a greater extent among which mainly indene, dihydronaphthalene, 1-methylindene, 3-methylindene, 2,3-dimethyldihydroindene, 1,2-dihydromethylnaphthalene.

The first fraction obtained from the latter distillation is particularly suitable for use as reagent containing naphthalenes to be used in step C of the integrated process described in the present invention.

The percentage of naphthalene and methylnaphthalenes, the two most important components (excluding the trimethylbenzene solvent) of the reagent mixture obtained as described above, may however be present in greater or smaller quantities with respect to the compositions indicated in this specific example in relation to the lower or higher concentration of naphthalene and methylnaphthalenes present in the raw naphthalene charge available.

Example 2

Preparation of the Catalyst to be Used in the Chemical Transformation Step C of Hydrocarbon Mixtures Prevalently Consisting of Naphthalene and/or Isomers of Methylnaphthalene and/or Isomers of Dimethylnaphthalene 2.4 g of sodium aluminate at 56% of $Al_2O_3$ are dissolved in 84 g of an aqueous solution of tetraethylammonium hydroxide at 35%. The limpid solution thus obtained is poured, under stirring, into 200 g of Ludox HS 40 colloidal silica. After brief stirring, a limpid, homogeneous gel is obtained, which is poured into an AISI 316 steel autoclave equipped with an anchor-type stirrer. The gel is crystallized under hydrothermal conditions at 160° C. for about 70 hours.

At the end, the autoclave is cooled, the solid separated from the mother liquor and washed with demineralized water until the washing water reaches a pH of less than 9.

The solid is then calcined at 550° C. in an atmosphere of air for 5 hours and re-dispersed in a solution of demineralized water and ammonium acetate. The concentration of ammonium acetate in said solution is such as to be present in the dispersion in a molar quantity equal to 5 times, and in any case in excess, with respect to the quantity of Aluminum present in the dispersed solid. During this operation the sodium present in the zeolite is substituted by the ammonium ion by means of ion exchange. This first exchange operation is followed by a washing operation, a second exchange with the same procedure as the first and another washing. The solid is then separated from the aqueous phase and dried at 100° C. for 3 hours in an atmosphere of air. The zeolite is thus obtained in ammonia form.

The zeolite in ammonia form thus obtained is dispersed in a solution of $(NH_4)_2HPO_4$ in demineralized water in a ratio of 1 gram of zeolite per 5 g of solution containing 0.005 g of $(NH_4)_2HPO_4$ salt. The dispersion thus obtained is kept under stirring for about 30 minutes at a temperature of 60° C. after which the solid is completely dried under vacuum. The solid thus obtained is then calcined in an atmosphere of air at 550° C. for 5 hours.

XRD analyses effected on the solid thus obtained indicate the presence of a single zeolitic crystalline phase of the MTW type whereas chemical analysis provides a molar ratio $SiO_2/Al_2O_3$ equal to 99 and a content of residual sodium of less than 50 ppm.

Various zeolite syntheses are subsequently effected, scrupulously following the procedure described above, in order to obtain a homogeneous quantity of product equal to about 200 g of ZSM-12 zeolite with the same structural, morphological and compositional characteristics indicated above.

A quantity equal to about 190.3 g of zeolite thus obtained is charged into a planetary type mixer together with 158.2 g of alumina p-bohemite and mixed for 24 minutes in order to reach a good uniformity between the powders.

A solution in demineralized water of acetic acid at 10% w/w is then fed to the mixer in a quantity equal to 300 cc over a period of time equal to 25 minutes, with the mixer running continuously.

The product thus obtained is directly fed to a roll extruder with holes having a diameter equal to about 2 mm from which pellets of catalyst are obtained, with a diameter equal to about 2 mm and a length equal to about 10 mm. The pellets are subsequently calcined in an atmosphere of air for 2 hours at 350° C. and for 3 hours at 550° C.

The end-catalyst thus obtained has a percentage of ZSM-12 zeolite referring to the total weight equal to 54.6% w/w, an extra-zeolite porosity equal to 0.545 cc/g and a radial crushing strength equal to 7 Kg.

Example 3

Chemical Transformation of Hydrocarbon Mixtures Prevalently Consisting of Naphthalene and/or Isomers of Methylnaphthalene and/or Isomers of Dimethylnaphthalene (Step C Without Methanol)

Four grams of catalyst obtained as described in example 2, are charged into the isotherm zone of a fixed bed catalyst reactor and inert quartz is subsequently fed above and below the catalytic bed to complete the reactor volume. The temperature of the reactor is raised to 200° C. in a stream of inert nitrogen at atmospheric pressure and the reactor is then cooled to room temperature.

A mixture of reagents consisting of 1,2,4-trimethylbenzene (1,2,4 TMB) and a naphthalene mixture containing naphthalene (NL), methylnaphthalenes (MNL) and dimethylnaphthalenes (DMN) wherein [1,2,4 TMB]/[total naphthalene moles in the reagent mixture]=10, is then fed to the reactor. The naphthalene mixture as such consists of 45.4% w/w of NL, 53% w/w of MNL and 1.6% w/w of DMN, and was obtained starting from a raw naphthalene charge of the FOK type subjected to distillation and subsequent pretreatment as described in example 1.

The reagent mixture consisting of the solvent and naphthalene mixture is fed with an overall WHSV equal to 2 h$^{-1}$ and operating so as to reach a pressure inside the reactor equal to 40 bars. When this pressure has been reached the reaction system is rapidly heated to a temperature of 350° C.

The reaction products are collected and analyzed by means of the GC technique. The sample collected over a period of 1 running hour of the reactor and after about 150 reaction hours indicated the composition specified in the table which also provides the composition of the initial mixture for comparative purposes.

| Naphthalene components | Feeding | Produced (after 148 hrs) |
|---|---|---|
| Naphthalene | 45.4% | 5.21% |
| Monomethylnaphthalenes | 53% | 28% |
| Dimethylnaphthalenes | 1.6% | 51.1% |
| 2,6 Dimethylnaphthalene | 0 | 15.4% |
| 2,7 Dimethylnaphthalene | 1.6% | 7.9% |
| Polymethylnaphthalenes | 0% | 15.7% |
| 2,6 DMN/2,7 DMN | | 1.95 |
| 2,6 DMN/Total DMN | | 30.1% |

After 148 hours the catalyst did not show evident signs of a reduction in activity or selectivity. During the test performance constancy was observed with the time on stream associated with high 2,6 DMN/2,7 DMN ratio values and of the 2,6 DMN fraction with respect to the total DMN.

Example 4

Chemical Transformation of Hydrocarbon Mixtures Prevalently Consisting of Naphthalene and/or Isomers of Methylnaphthalene and/or Isomers of Dimethylnaphthalene (Step C with Methanol)

Four grams of catalyst obtained as described in example 2, are charged into the isotherm zone of a fixed bed catalyst reactor and inert quartz is subsequently fed above and below the catalytic bed to complete the reactor volume. The temperature of the reactor is raised to 200° C. in a stream of inert nitrogen at atmospheric pressure and the reactor is then cooled to room temperature.

A mixture of reagents is then fed to the reactor, consisting of methanol, 1,2,4-trimethylbenzene (1,2,4 TMB) and a naphthalene mixture containing naphthalene, methylnaphthalenes, dimethylnaphthalenes and polymethylnaphthalenes wherein [1,2,4 TMB]/[total naphthalene moles in the reagent mixture]=10 and [Methanol]/[total naphthalene moles in the reagent mixture]=0.1.

The naphthalene mixture was obtained starting from a raw naphthalene charge of the FOK type subjected to distillation and subsequent pretreatment as described in example 1 and subsequently adding a certain quantity of dimethylnaphthalenes so as to reach the end feeding-compositions indicated in the table.

The overall feeding of the reagent mixture is effected with a WHSV equal to 10 h$^{-1}$ and operating so as to reach a pressure inside the reactor equal to 40 bars. When this pressure has been reached the reaction system is rapidly heated to a temperature of 350° C. The reaction products are collected and analyzed by means of the GC technique. The sample collected over a period of 1 running hour of the reactor and after about 150 reaction hours indicated the composition specified in the table which also provides the composition of the initial mixture for comparative purposes.

| Naphthalene components | Feeding | Produced (after 148 hrs) |
|---|---|---|
| Naphthalene | 4.9% | 3.1% |
| Monomethylnaphthalenes | 40.6% | 28% |
| Dimethylnaphthalenes | 43.1% | 51.3% |
| 2,6 Dimethylnaphthalene | 6.5% | 14% |
| 2,7 Dimethylnaphthalene | 7.8% | 9% |
| Polymethylnaphthalenes | 11.4% | 17.8% |
| 2,6 DMN/2,7 DMN | 0.83% | 1.56 |
| 2,6 DMN/Total DMN | 15.1% | 27.3% |

Example 5

Separation of Hydrocarbon Mixtures Prevalently Consisting of Dimethylnaphthalenes and Chemical Transformation (Isomerization) of One of the Fractions thus Obtained (Step H and Step I)

The following example describes, for purely illustrative purposes, the distillation step (H) and isomerization step (I) included in the integrated process, object of the present invention without limiting its scope in any way.

A sample of prevalently naphthalene hydrocarbons with a boiling point ranging from 246 to 260° C., obtained by distillation in an experimental laboratory device equipped with several distillation columns starting from a reaction product as conducted in example 4, is preheated to 185° C. and fed in continuous to the 30$^{th}$ plate upwards of a laboratory column having 70 perforated plates with a diameter of 50 mm. The residual pressure at the head of the column is equal to 85 mmHg and each plate produces a pressure drop of 0.5 mmHg. The flow-rate of the hydrocarbons fed to the column is equal to 150 ml/h. Maintaining an L/D volume reflux ratio of 7 and removing from the head and bottom of the column 105 and 45 l/h respectively of product, a regime condition is reached, characterized by a temperature at the head and bottom of 172 and 197° C. respectively and the compositions indicated in the table.

| Naphthalene components | Feeding | Head | Bottom |
|---|---|---|---|
| Monomethylnaphthalenes | 2.52% w | 3.43% w | 0.00% w |
| 2,6-Dimethylnaphthalene | 30.49% w | 40.67% w | 10.40% w |
| 1,6-Dimethylnaphthalene | 24.75% w | 12.89% w | 47.08% w |
| 1,5-Dimethylnaphthalene | 3.77% w | 0.32% w | 10.79% w |
| Other Dimethylnaphthalenes | 35.20% w | 40.23% w | 25.29% w |
| Unknown | 3.28% w | 2.46% w | 6.44% w |
| 2,6 DMN/(1,6 + 1,5 DMN) | 1.07 | 3.08 | 0.18 |

Four grams of catalyst obtained as described in example 2, are charged into the isotherm zone of a fixed bed catalyst reactor and inert quartz is subsequently fed above and below the catalytic bed to complete the reactor volume. The temperature of the reactor is raised to 200° C. in a stream of inert nitrogen at atmospheric pressure and the reactor is then cooled to room temperature.

The mixture of prevalently naphthalene hydrocarbons obtained as bottom product in the distillation described above in the previous example, is then fed to the reactor.

The reagent mixture is fed with an overall WHSV equal to 16 h$^{-1}$ and operating so as to reach a pressure inside the reactor equal to 40 bars. When this pressure has been reached the reaction system is rapidly heated to a temperature of 350° C.

The reaction products are collected and analyzed by means of the GC technique. The sample collected over a period of 1 running hour of the reactor and after about 150 reaction hours indicated the composition specified in the table which also provides the composition of the initial mixture for comparative purposes.

| Naphthalene components | Feeding | Produced (after 150 hrs) |
| --- | --- | --- |
| Monomethylnaphthalenes | 0.00% w | 0.85% w |
| 2,6-Dimethylnaphthalene | 10.40% w | 30.39% w |
| 1,6-Dimethylnaphthalene | 47.08% w | 31.34% w |
| 1,5-Dimethylnaphthalene | 10.79% w | 5.09% w |
| Other Dimethylnaphthalenes | 25.29% w | 24.76% w |
| Unknown | 6.44% w | 7.57% w |
| 2,6 DMN/(1,6 + 1,5 DMN) | 0.18 | 0.83 |

After 150 hours the catalyst did not shown any signs of reduction in activity or selectivity.

Example 6

Chemical Transformation of Hydrocarbon Mixtures Prevalently Consisting of Dimethylnaphthalene Isomers (Step F)

Four grams of a catalyst based on beta zeolite called A1 and prepared according to the procedure described in example 4 of patent EP 847802, are charged into the isotherm zone of a fixed bed catalyst reactor and inert quartz is subsequently fed above and below the catalytic bed to complete the reactor volume. The temperature of the reactor is raised to 200° C. in a stream of inert nitrogen at atmospheric pressure and the reactor is then cooled to room temperature.

A mixture of reagents consisting of Toluene and a naphthalene mixture containing dimethylnaphthalene isomers wherein [Toluene]/[total naphthalene moles in the reagent mixture]=5, is then fed to the reactor.

The naphthalene mixture containing dimethylnaphthalene isomers derives from the crystallization mother liquor of effluent dimethylnaphthalenes from the reaction section of the integrated process claimed herein. The overall feeding of the reagent mixture is effected with a WHSV equal to 0.7 h$^{-1}$ and operating so as to reach a pressure inside the reactor equal to 40 bars. When this pressure has been reached the reaction system is rapidly heated to a temperature of 310° C. The reaction products are collected and analyzed by means of the GC technique. The sample collected over a period of 1 running hour of the reactor and after about 150 reaction hours indicated the composition specified in the table which also provides the composition of the initial mixture for comparative purposes.

| Naphthalene components | Feeding | Produced (after 157 hrs) |
| --- | --- | --- |
| Naphthalene | — | 8.20% |
| Monomethylnaphthalenes | — | 32.00% |
| Dimethylnaphthalenes | 100% | 37.30% |
| 2,6 Dimethylnaphthalene | 15% | 10.03% |
| 2,7 Dimethylnaphthalene | 18.5% | 6.90% |
| Polymethylnaphthalenes | — | 22.50% |
| 2,6 DMN/2,7 DMN | 0.81 | 1.45 |
| 2,6 DMN/Total DMN | 15% | 26.89% |

Example 6 Bis

Chemical Transformation of Hydrocarbon Mixtures Prevalently Consisting of Dimethylnaphthalene Isomers (Step F)

Four grams of the same catalyst used in example 6 and prepared according to the procedure described in example 4 of patent EP 847802 are charged into the isotherm zone of a fixed bed catalyst reactor and inert quartz is subsequently fed above and below the catalytic bed to complete the reactor volume. The temperature of the reactor is raised to 200° C. in a stream of inert nitrogen at atmospheric pressure and the reactor is then cooled to room temperature.

A mixture of reagents consisting of a naphthalene fraction and a naphthalene mixture containing dimethylnaphthalene isomers wherein [naphthalene]/[dimethylnaphthalenes]=2, is then fed to the reactor.

The naphthalene fraction comes from the separation section by means of distillation of the integrated process claimed herein.

The naphthalene mixture containing dimethylnaphthalene isomers derives from the crystallization mother liquor of isomeric mixtures of effluent dimethylnaphthalenes from the reaction section of the integrated process claimed herein.

The overall feeding of the reagent mixture is effected with a WHSV equal to 1 h$^{-1}$ and operating so as to reach a pressure inside the reactor equal to 40 bars. When this pressure has been reached the reaction system is rapidly heated to a temperature of 310° C. The reaction products are collected and analyzed by means of GC. The sample collected over a period of 1 running hour of the reactor and after about 150 reaction hours indicated the composition specified in the table which also provides the composition of the initial mixture for comparative purposes.

| Naphthalene components | Feeding | Produced (after 145 hrs) |
| --- | --- | --- |
| Naphthalene | 66.4% | 40.5% |
| Monomethylnaphthalenes | — | 34.3% |
| Dimethylnaphthalenes | 33.6% | 18.6% |
| 2,6 Dimethylnaphthalene | 5.04% | 5.0% |
| 2,7 Dimethylnaphthalene | 6.22% | 3.44% |
| Polymethylnaphthalenes | — | 6.60% |
| 2,6 DMN/2,7 DMN | 0.81 | 1.45 |
| 2,6 DMN/Total DMN | 15% | 26.91% |

Example 7

Extraction and Purification of 2,6 DMN from Isomeric Mixtures (Step E)

3 Kg of an isomeric mixture of dimethylnaphthalenes obtained by the distillation of a typical reaction effluent of the integrated process described herein and 0.75 Kg of methanol are charged into a 5 liter stirred reactor equipped with a jacket. The composition of the isomeric mixture is as follows: 2,6 dimethylnaphthalene 27.6%, 2,7 dimethylnaphthalene 15.9%, 1,6 dimethylnaphthalene 29.1%, other naphthalene components 29.1%.

The reactor is heated until the contents have reached a temperature of 55° C., subsequently cooled to 41° C. to allow the crystallization to be triggered and then brought to 46° C. at which the crystallization initiates, in the presence of a few 2,6 dimethylnaphthalene crystals. A cooling ramp is established, starting from a temperature of 46° C., to bring the contents of the reactor to a temperature of 25° C. over a period of 6 hours.

At the end, the reactor is emptied by filtering the suspension in a porous filter of the G2 type, recovering 0.96 Kg of wet solid panel and 2.79 Kg of crystallization mother liquor solution. The wet solid panel has a ratio between solid and wetting liquid equal to 1/1.14 whereas the composition of the solid panel without the wetting liquid is as follows: 2,6 dimethylnaphthalene 98.8t, 2,7 dimethylnaphthalene 1.2%.

The composition of the wet solid panel referring to dimethylnaphthalene isomers alone, is as follows: 2,6 dimethylnaphthalene 59.5%, 2,7 dimethylnaphthalene 9.31%, 1,6 dimethylnaphthalene 15.1%, other dimethylnaphthalene isomers 16%.

The composition of the crystallization mother liquor referring to dimethylnaphthalene isomers alone, is as follows: 2,6 dimethylnaphthalene 15%, 2,7 dimethylnaphthalene 18.5%, 1,6 dimethylnaphthalene 32.2%, other dimethylnaphthalene isomers 34.2%.

In FIG. 4 the operations described so far are indicated as step $E_a$.

The wet solid panel is then washed with about 1.6 Kg of methanol at a temperature of about 20° C., recovering 1.680 Kg of washing liquid and 0.880 Kg of wet solid panel.

The wet solid panel has a ratio between solid and washing liquid equal to 1/0.96 whereas the composition of the solid panel without the washing liquid is as follows: 2,6 dimethylnaphthalene 98.8%, 2,7 dimethylnaphthalene 1.2%.

The composition of the wet solid panel referring to dimethylnaphthalene isomers alone, is as follows: 2,6 dimethylnaphthalene 86%, 2,7 dimethylnaphthalene 3.86%, 1,6 dimethylnaphthalene 4.93%, other dimethylnaphthalene isomers 5.24%.

The composition of the washing liquid referring to dimethylnaphthalene isomers alone, is as follows: 2,6 dimethylnaphthalene 15.2%, 2,7 dimethylnaphthalene 18.5%, 1,6 dimethylnaphthalene 32.2%, other dimethylnaphthalene isomers 34.2%.

The wet solid panel is then washed a second time with about 1.4 Kg of methanol at a temperature of about 20° C., recovering 1.547 Kg of washing liquid and 0.73 Kg of wet solid panel.

The wet solid panel has a ratio between solid and washing liquid equal to 1/0.69 whereas the composition of the solid panel without the washing liquid is as follows: 2,6 dimethylnaphthalene 98.8%, 2,7 dimethylnaphthalene 1.2%.

The composition of the wet solid panel referring to dimethylnaphthalene isomers alone, is as follows: 2,6 dimethylnaphthalene 96.3%, 2,7 dimethylnaphthalene 1.7%, 1,6 dimethylnaphthalene 0.94%, other dimethylnaphthalene isomers 1%.

The composition of the washing liquid referring to dimethylnaphthalene isomers alone, is as follows: 2,6 dimethylnaphthalene 27.1%, 2,7 dimethylnaphthalene 16%, 1,6 dimethylnaphthalene 27.6%, other dimethylnaphthalene isomers 29.3%.

In FIG. 4 the operations described so far are indicated as step $E_b$.

The wet solid panel is then re-dissolved with about 4.9 Kg of methanol at a temperature of 64° C. under stirring. Starting from a temperature of 64° C., a cooling ramp is established to bring the contents of the reactor to a temperature of 20° C. over a period of 3 hours.

At the end, the reactor is emptied by filtering the suspension in a porous filter of the G2 type, recovering 0.403 Kg of wet solid panel and 5.23 Kg of crystallization mother liquor solution.

The wetting liquid contained in the wet solid panel has the same composition as the re-crystallization mother liquor and consists of 98.5% of methanol.

The composition of the wet solid panel referring to dimethylnaphthalene isomers alone, is as follows: 2,6 dimethylnaphthalene 99.8%, 2,7 dimethylnaphthalene 0.19%, 1,6 dimethylnaphthalene 0.005%, other dimethylnaphthalene isomers 0.005%.

The composition of the crystallization mother liquor referring to dimethylnaphthalene isomers alone, is as follows: 2,6 dimethylnaphthalene 80.6%, 2,7 dimethylnaphthalene 8.64%, 1,6 dimethylnaphthalene 5.21%, other dimethylnaphthalene isomers 5.54%.

The wet solid panel is then charged into a laboratory flask equipped with a heating jacket where the residual methanol is evaporated, at a temperature of 90° C., in a quantity equal to 0.0336 Kg.

The quantity of solid recovered is equal to 0.369 Kg having the following composition: 2,6 dimethylnaphthalene 99.8%, 2,7 dimethylnaphthalene 0.19%, 1,6 dimethylnaphthalene 0.005%, other dimethylnaphthalene isomers 0.005%.

The recovery yield of 2,6 dimethylnaphthalene is equal to 44.5%.

In FIG. 4 the operations described so far are indicated as step $E_c$.

This example describes only one of the possible configurations of the crystallization section of the integrated process claimed herein. In particular, a laboratory experiment has been described in which there is no recovery or re-use either of the solvent or crystallization and/or washing mother liquor. The following example, on the other hand, describes another possible configuration of the crystallization section of the integrated process claimed herein.

Example 8

Extraction and Purification of 2,6 DMN from Isomeric Mixtures (Step E)

Figure 5:
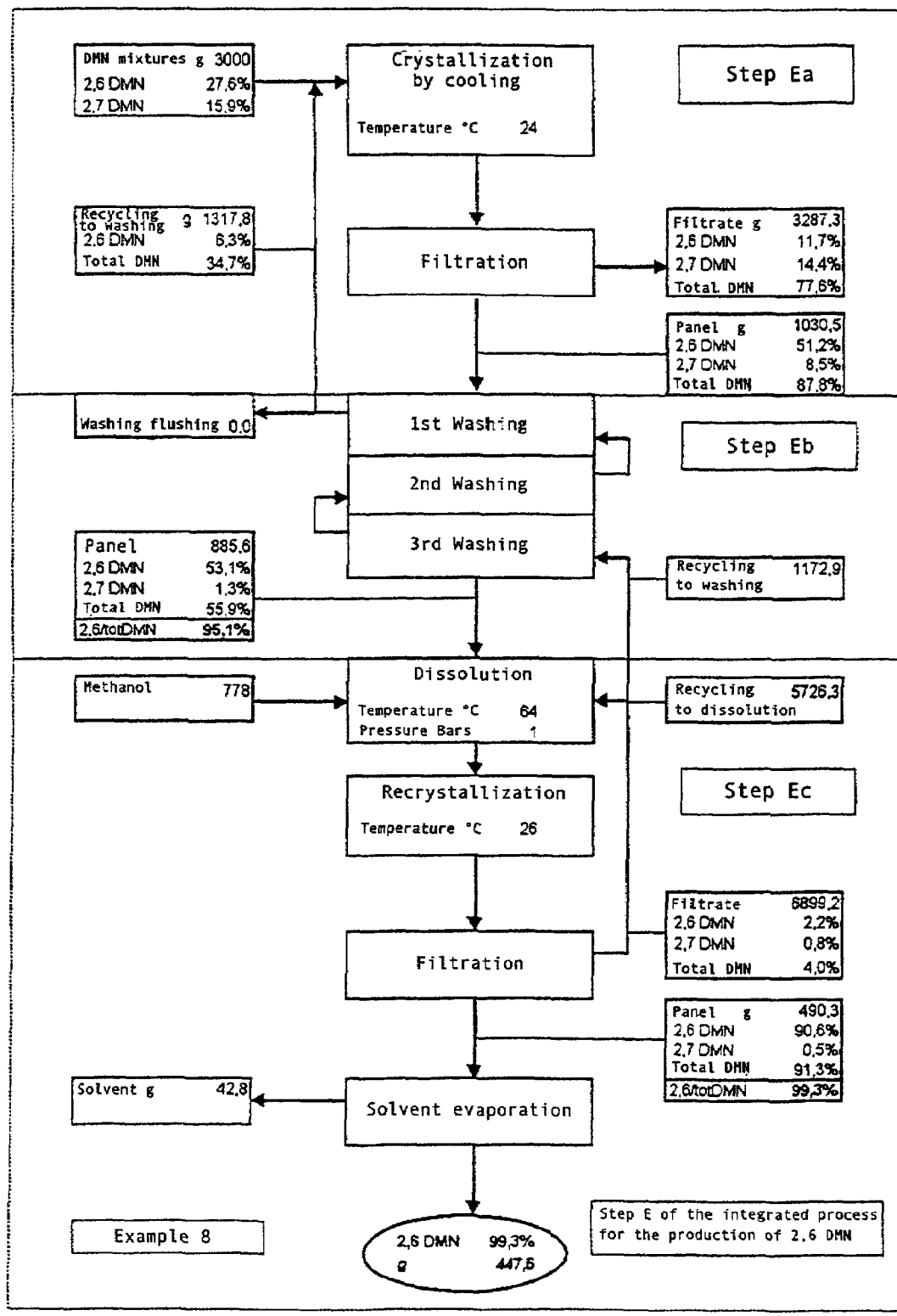
FIG. 5 shows the extraction and purification of 2,6-dimethylnaphthalene described in Example 8.

This experimental test describes another possible configuration for the crystallization section. In particular, an experimental test is described, characterized by the reuse of the crystallization mother liquor and of the washing water formed in the various steps. FIG. 5 shows a scheme of step E with a quantified balance of the various steps of which it is composed.

The following experimental test therefore represents a closed cycle and in countercurrent, obtained as described hereunder.

In step $E_a$ the crystallization is carried out re-using the liquid obtained in the 1$^{st}$ of the 3 washings effected in step $E_b$.

In step $E_b$ the liquid used in each of the various washings comes from the subsequent washing whereas that used in the 3$^{rd}$ washing comes, on the other hand, from step $E_c$.

In step $E_c$ fresh methanol is fed in the re-dissolution step of the solid coming from step $E_b$ whereas the liquid deriving from the filtration is partly re-used in step $E_b$ and partly again in the re-dissolution passage of the solid coming from step $E_b$.

3 Kg of an isomeric mixture of dimethylnaphthalenes obtained from the distillation of a typical reaction effluent of the integrated process described herein and 1.318 Kg of liquid coming from the 1$^{st}$ washing of the subsequent step $E_b$, are charged into a 5 liter stirred reactor equipped with a jacket.

The composition of the isomeric mixture is as follows: 2,6 dimethylnaphthalene 27.6%, 2,7 dimethylnaphthalene 15.9%, 1,6 dimethylnaphthalene 27.4%, other dimethylnaphthalene isomers 29.1%.

The reactor is heated until the contents have reached a temperature of 55° C., subsequently cooled to 41° C. to allow the crystallization to be triggered and then brought to 46° C. at which the crystallization initiates, in the presence of a few 2,6 dimethylnaphthalene crystals. A cooling ramp is established, starting from a temperature of 46° C., to bring the contents of the reactor to a temperature of 240° C. over a period of 6 hours.

At the end, the reactor is emptied by filtering the suspension in a porous filter of the G2 type, recovering 1.030 Kg of wet solid panel and 3.287 Kg of crystallization mother liquor solution. The wet solid panel has a ratio between solid and wetting liquid equal to 1/1.2 whereas the composition of the solid panel without the wetting liquid is as follows: 2,6 dimethylnaphthalene 98.6%, 2,7 dimethylnaphthalene 1.4%.

The composition of the wet solid panel referring to dimethylnaphthalene isomers alone, is as follows: 2,6 dimethylnaphthalene 58.3%, 2,7 dimethylnaphthalene 9.7%, 1,6 dimethylnaphthalene 15.5%, other dimethylnaphthalene isomers 16.5%.

The composition of the crystallization mother liquor referring to dimethylnaphthalene isomers alone, is as follows: 2,6 dimethylnaphthalene 15%, 2,7 dimethylnaphthalene 18.6%, 1,6 dimethylnaphthalene 32.1%, other dimethylnaphthalene isomers 34.2%.

In FIG. 5 the operations described so far are indicated in step $E_a$.

The wet solid panel is then washed with about 1.219 Kg of liquid coming from the $2^{nd}$ washing of step $E_b$ at a temperature of about 26° C., recovering 1.318 Kg of washing liquid and 0.932 Kg of wet solid panel.

The wet solid panel has a ratio between solid and washing liquid equal to 1/1 whereas the composition of the solid panel without the washing liquid is as follows: 2,6 dimethylnaphthalene 98.6%, 2,7 dimethylnaphthalene 1.4%.

The composition of the wet solid panel referring to dimethylnaphthalene isomers alone, is as follows: 2,6 dimethylnaphthalene 77.9%, 2,7 dimethylnaphthalene 5.8%, 1,6 dimethylnaphthalene 7.9%, other dimethylnaphthalene isomers 8.4%.

The composition of the washing liquid referring to dimethylnaphthalene isomers alone, is as follows: 2,6 dimethylnaphthalene 18.2%, 2,7 dimethylnaphthalene 18.6%, 1,6 dimethylnaphthalene 30.6%, other dimethylnaphthalene isomers 32.6%.

The wet solid panel is then washed a second time with about 1.173 Kg of liquid coming from the $3^{rd}$ washing of step $E_b$ at a temperature of about 26° C., recovering 1.219 Kg of washing liquid and 0.886 Kg of wet solid panel.

The wet solid panel has a ratio between solid and washing liquid equal to 1/0.9 whereas the composition of the solid panel without the washing liquid is as follows: 2,6 dimethylnaphthalene 98.6%, 2,7 dimethylnaphthalene 1.4%.

The composition of the wet solid panel referring to dimethylnaphthalene isomers alone, is as follows: 2,6 dimethylnaphthalene 89.9%, 2,7 dimethylnaphthalene 3.4%, 1,6 dimethylnaphthalene 3.2%, other dimethylnaphthalene isomers 3.4%.

The composition of the washing liquid referring to dimethylnaphthalene isomers alone, is as follows: 2,6 dimethylnaphthalene 24.8%, 2,7 dimethylnaphthalene 18.8%, 1,6 dimethylnaphthalene 27.3%, other dimethylnaphthalene isomers 29.1%.

The wet solid panel is then washed a third time with about 1.173 Kg of liquid coming from the subsequent step $E_c$ at a temperature of about 26° C., recovering 1.173 Kg of washing liquid and 0.886 Kg of wet solid panel.

The wet solid panel has a ratio between solid and washing liquid equal to 1/0.9 whereas the composition of the solid panel without the washing liquid is as follows: 2,6 dimethylnaphthalene 98.6%, 2,7 dimethylnaphthalene 1.4%.

The composition of the wet solid panel referring to dimethylnaphthalene isomers alone, is as follows: 2,6 dimethylnaphthalene 95.1%, 2,7 dimethylnaphthalene 2.4%, 1,6 dimethylnaphthalene 1.2%, other dimethylnaphthalene isomers 1.3%.

The composition of the washing liquid referring to dimethylnaphthalene isomers alone, is as follows: 2,6 dimethylnaphthalene 38.0%, 2,7 dimethylnaphthalene 19.1%, 1,6 dimethylnaphthalene 20.8%, other dimethylnaphthalene isomers 22.1%.

In FIG. 5 the operations described so far are indicated in step $E_b$.

The wet solid panel is then re-dissolved with about 6.504 Kg of a mixture consisting of 0.778 Kg of fresh methanol and 5.726 Kg of liquid obtained from the subsequent filtration passage of step $E_c$, at a temperature of 64° C. under stirring. Starting from a temperature of 64° C., a cooling ramp is established to bring the contents of the reactor to a temperature of 26° C. over a period of 3 hours.

At the end, the reactor is emptied by filtering the suspension in a porous filter of the G2 type, recovering 0.490 Kg of wet solid panel and 6.899 Kg of re-crystallization mother liquor solution.

The wetting liquid contained in the wet solid panel has the same composition as the re-crystallization mother liquor and consists of 96.0% of methanol.

The composition of the wet solid panel referring to dimethylnaphthalene isomers alone, is as follows: 2,6 dimethylnaphthalene 99.3%, 2,7 dimethylnaphthalene 0.6%, 1,6 dimethylnaphthalene 0.05%, other dimethylnaphthalene isomers 0.05%.

The composition of the re-crystallization mother liquor referring to dimethylnaphthalene isomers alone, is as follows: 2,6 dimethylnaphthalene 55.3%, 2,7 dimethylnaphthalene 19.5%, 1,6 dimethylnaphthalene 12.2%, other dimethylnaphthalene isomers 12.9%.

The wet solid panel is then charged into a laboratory flask equipped with a heating jacket where the residual methanol is evaporated, at a temperature of 90° C., in a quantity equal to 0.043 Kg.

The quantity of solid recovered is equal to 0.447 Kg having the following composition: 2,6 dimethylnaphthalene 99.3%, 2,7 dimethylnaphthalene 0.6%, 1,6 dimethylnaphthalene 0.05%, other dimethylnaphthalene isomers 0.05%.

The recovery yield of 2,6 dimethylnaphthalene is equal to 53.6%.

In FIG. 5 the operations described so far are indicated in step $E_c$.

The invention claimed is:

1. A process for the preparation of high purity 2,6-dimethylnaphthalene starting from hydrocarbon mixtures comprising naphthalene and/or isomers of methylnaphthalene and/or isomers of dimethylnaphthalene and/or isomers of polymethylnaphthalene, and from a methylating agent which are reacted in a benzene solvent in the presence of a catalyst comprising a zeolite, the process comprising:

enriching, by means of distillation, of the hydrocarbon mixture of interest with the consequent production of a first hydrocarbon fraction comprising a high concentration of the above naphthalene compounds and a second fraction comprising prevalently non-naphthalene compounds;

treating the mixture of naphthalene compounds obtained in the previous step with an acid catalyst in a methylated benzene solvent;

alkylating the mixture comprising said solvent and said naphthalene compounds by reaction with a methylating agent in a benzene solvent in the presence of a catalyst comprising a zeolite;

transalkylating the hydrocarbon mixture consisting of naphthalene and/or isomers of dimethylnaphthalene and/or isomers of polymethylnaphthalene, carried out in the presence of a solid acid catalyst, which may be based on acid zeolites, and a mixture of methylated benzene solvents consisting essentially of benzene, toluene and xylenes with an overall molar ratio between methyls and benzene ring of less than 2, in order to obtain a hydrocarbon mixture characterized by a higher concentration of methylnaphthalene isomers;

at least one separating phase, by distillation, of the mixtures resulting from said alkylating or said transalkylating;

at least one purifying phase of the mixtures coming from said alkylating or said translkylating, by means of crystallization operations and washings carried out in the presence of a low molecular weight alcohol selected from the group consisting of methanol, ethanol, propanol, and a glycol, in order to obtain the separation of the 2,6-dimethyl-naphtalene from the fraction prevalently consisting of dimethylnaphtalene.

2. The process for the preparation of 2,6-dimethylnaphthalene according to claim 1, wherein the hydrocarbon mixture coming from said treating is separated into two fractions, one comprising naphthalene compounds and the other comprising heavy non-naphthalene compounds.

3. The process according to claim 1, wherein the methylated benzene solvent in said treating is selected from the group consisting of toluene, xylene and trimethylbenzene.

4. The process according to claim 1, wherein the acid catalyst in said treating is a solid catalyst selected from the group consisting of clays, zeolites, sulfonated zirconia, acid resins, aluminas, silico-alumina, oxides and heteropolyacids.

5. The process for the preparation of 2,6-dimethylnaphthalene according to claim 1 wherein the methylating agent comprises methanol.

6. The process according to claim 1, wherein in said transalkylating, the hydrocarbon mixture comprises prevalently isomers of dimethylnaphthalene and/or isomers of polymethylnaphthalene.

7. The process according to claim 6, wherein in said transalkylating the hydrocarbon mixture comprises prevalently isomers of dimethylnaphthalene and isomers of polymethylnaphthalene.

8. The process according to claim 1, wherein the solid acid catalyst in said transalkylating is a large pore zeolite.

9. The process according to claim 8, wherein the solid acid catalyst is a beta zeolite, a Y zeolite, or a ZSM-12 zeolite.

10. The process according to claim 1, wherein said low molecular weight alcohol is methanol.

11. The process according to claim 1, wherein said transalkylating is transforming the hydrocarbon mixture consisting of isomers of dimethylnalhthalene and/or isomers of polymthylnaphthalene.

12. A process for the preparation of high purity 2,6-dimethylnaphthalene starting from hydrocarbon mixtures comprising naphthalene and/or isomers of methylnaphthalene and/or isomers of dimethylnaphthalene and/or isomers of polymethylnaphthalene, and from a methylating agent which are reacted in a benzene solvent in the presence of a catalyst comprising a zeolite, the process comprising A. enriching, by means of distillation, of the hydrocarbon mixture of interest with the consequent production of a first hydrocarbon fraction comprising a high concentration of the above naphthalene compounds and a second fraction comprising prevalently non-naphthalene compounds;

B. treating the mixture of naphthalene compounds obtained in the previous step with an acid catalyst in a methylated benzene solvent;

C. the obtained mixture comprising methylated benzene solvent and naphthalene compounds is reacted with a methylating agent in the presence of a catalyst consisting of ZSM-12 zeolite and an inorganic binder in a mixture of methylated benzene solvents with an overall molar ratio between methyls and aromatic rings equal to or higher than 2;

D. a mixture coming from step C and also from step F and step G is separated, by distillation, with the production of the following six fractions:
  $b_1$) water and benzene solvents,
  $b_2$) methyl-benzenes,
  $b_3$) naphthalene,
  $b_4$) methylnaphthalene isomers,
  $b_5$) dimethylnaphthalene isomers, and
  $b_6$) polymethylnaphthalenes; and
  $b_1$ is fed, after removal of water, to step B and step F,
  $b_2$ is fed to step B and step C;
  $b_3$ is fed to step F and step C,
  $b_4$ is fed to step C,
  $b_5$ is fed to step E, and
  $b_6$ is fed to step F and step C;

E. $b_5$ is purified by crystallization and washing and consequent formation of two fractions:
  $d_1$) 2,6-dimethylnaphthalene, and
  $d_2$) 2,6-dimethylnaphthalene isomers; and
  $d_2$ is fed to step C and step F;

F. transalkylating in the presence of methylated benzene solvents with an overall molar ratio between methyls and benzene rings of less than 2 with recycling of the reaction product to step D and, partly, to step G; and G. a mixture obtained in step F is distilled with consequent production of the following fractions:
  $g_1$) comprising benzene solvents,
  $g_2$) comprising dimethylnaphthalene isomers, and
  subsequent recycling of $g_1$ to step D and of $g_2$ to step F.

13. The process according to claim 12, wherein the methylated benzene solvent in said treating, is selected from the group consisting of toluene, xylene and trimethylbenzene.

14. The process according to claim 12, wherein the acid catalyst in said treating is a solid catalyst selected from the group consisting of clays, zeolites, sulfonated zirconia, acid resins, aluminas, silico-alumina, oxides and heteropolyacids.

15. The process according to claim 12 wherein the methylating agent comprises methanol.

16. The process according to claim 12, wherein said transalkylating is transforming the hydrocarbon mixture consisting of isomers of dimethylnaphthalene and/or isomers of polymethylnaphthalene.

17. A process for the preparation of high purity 2,6-dimethylnaphthalene starting from hydrocarbon mixtures comprising naphthalene and/or isomers of methylnaphthalene and/or isomers of dimethylnaphthalene and/or isomers of polymethylnaphthalene, and from a methylating agent which are reacted in a benzene solvent in the presence of a catalyst comprising a zeolite, the process comprising
  A. enriching, by means of distillation, of the hydrocarbon mixture of interest with the consequent production of a first hydrocarbon fraction comprising a high concentration of the above naphthalene compounds and a second fraction comprising prevalently non-naphthalene compounds;
  B. treating the mixture of naphthalene compounds obtained in the previous step with an acid catalyst in a methylated benzene solvent;
  C. the obtained mixture comprising methylated benzene solvent and naphthalene compounds is reacted with a methylating agent in the presence of a catalyst comprising ZSM-12 zeolite and a inorganic ligand in a mixture of methylated benzene solvents with an overall molar ratio between methyls and aromatic rings equal to or higher than 2;
  D. a mixture coming from step C and also from step G is separated, by distillation, with the production of the following six fractions:
    $b_1$) water and benzene solvents,
    $b_2$) methyl-benzenes,
    $b_3$) naphthalene,
    $b_4$) methylnaphthalene isomers,
    $b_5$) dimethylnaphthalene isomers, and
    $b_6$) polymethylnaphthalenes;
    followed by feeding $b_1$, after removal of water, to step B and step F,
    feeding $b_2$ to step B and step C;
    feeding $b_3$ to step F and step C,
    feeding $b_4$ to step C,
    feeding $b_5$ to step H, and
    feeding $b_6$ to step F and step C;
  E. a first fraction coming from step H comprising a mixture of dimethylnaphthalene isomers and comprising a high concentration of the 2,6 isomer is purified with consequent formation of the following fractions:
    $c_1$) 2,6-dimethylnaphthalene,
    $c_2$) dimethylnaphthalene isomers, and
    subsequently feeding $c_2$ to step C and step F;
  F. transalkylating in the presence of methylated benzene solvents with an overall molar ratio between methyls and benzene rings of less than 2 with recycling of the reaction product to step G;
  G. a reaction mixture from step F is separated by distillation, with consequent production of the following fractions:
    $e_1$) solvents, naphthalene, methylnaphthalene isomers,
    $e_2$) dimethylnaphthalene isomers, polymethylnaphthalene, and
    sending $e_1$ to step D and $e_2$ to step F;
  H. $b_5$ fraction is separated with consequent production of the following fractions:
    $f_1$) dimethylnaphthalene isomers with a concentration greater than 2.6,
    $f_2$) dimethylnaphthalene isomers with a concentration lower than 2.6, and
    $f_1$ is sent to step E and $f_2$ to step I;
  I. isomerizing $f_2$ and sending the reaction product to step H.

18. The process according to claim 17, wherein the methylated benzene solvent in said treating, is selected from the group consisting of toluene, xylene and trimethylbenzene.

19. The process according to claim 17, wherein the acid catalyst in treating said treating is a solid catalyst selected from the group consisting of clays, zeolites, sulfonated zirconia, acid resins, aluminas, silico-alumina, oxides and heteropolyacids.

20. The process according to claim 17, wherein the methylating agent comprises methanol.

21. The process according to claim 17, wherein said transalkylating is transforming the hydrocarbon mixture consisting of isomers of dimethylnaphthalene and/or isomers of polymethylnaphthalene.

22. A process for the preparation of high purity 2,6-dimethylnaphthalene starting from hydrocarbon mixtures comprising naphthalene and/or isomers of methylnaphthalene and/or isomers of dimethylnaphthalene and/or isomers of polymethylnaphthalene, and from a methylating agent which are reacted in a benzene solvent in the presence of a catalyst comprising a zeolite, the process comprising:
  A. enriching, by distillation, a hydrocarbon mixture comprising naphthalene and/or isomers of methylnaphthalene and/or isomers of dimethylnaphthalene and/or isomers of polymethylnaphthalene to obtain a first hydrocarbon fraction comprising a higher concentration of said naphthalene compounds and a second fraction comprising primarily non-naphthalene compounds;
  B. purifying the hydrocarbon mixture obtained in step A comprising naphthalene and/or isomers of methylnaphthalene and/or isomers of dimethylnaphthalene and/or isomers of polymethylnaphthalene, by reacting said mixture with a solid acid catalyst in the presence of a methylated benzene solvent, followed by separating the resulting mixture into a first fraction consisting of the benzene solvent and said naphthalene compounds and a second hydrocarbon fraction comprising prevalently of heavy non-naphthalene compounds, initially present or formed in said purification step;
  C. alkylating a hydrocarbon mixture comprising naphthalene and/or isomers of methylnaphthalene and/or isomers of dimethylnaphthalene and/or isomers of polymethylnaphthalene, to produce an effluent comprising a hydrocarbon mixture enriched in 2,6-dimethylnaphthalene isomer, wherein the alkylating is carried out in the presence of a methylating agent, a methylated benzene solvent, or mixtures of various methylated benzene solvents, starting from toluene up to hexamethylbenzene, a ZSM-12 zeolite and an inorganic ligand, wherein said mixture of methylated benzene solvents is such as to have an overall molar ratio between methyls and aromatic benzene ring equal to or higher than 2;
  D. separating, by distillation, a mixture comprising an aqueous phase, benzene and mixtures of various methylated benzene solvents, naphthalene and/or isomers of methylnaphthalene and/or isomers of dimethylnaphthalene and/or isomers of polymethylnaphthalene obtained from step C and steps F and G, to obtain a first fraction comprising prevalently water and benzene, toluene and xylenes,
    wherein an overall molar ratio between methyls and benzene ring is less than 2,
      a second fraction comprising prevalently tri-, tetra-, penta- and hexamethylbenzene,
    wherein an overall molar ratio between methyls and benzene ring equal to or higher than 2 and preferably higher than 3,
      a third fraction comprising prevalently naphthalene,
      a fourth fraction comprising prevalently methylnaphthalene isomers, a fifth fraction comprising prevalently isomers of dimethylnaphthalene comprising the 2,6 dimethylnaphthalene isomer, a sixth fraction comprising prevalently polymethylnaphthalenes, wherein the first fraction, after separation and removal of water by demixing, is partly sent to step B and partly to the step F, the second fraction is partly sent to step B and partly to step C, the third fraction is partly sent to step F and partly to step C, the fourth fraction is sent to step C, the fifth fraction is sent to step E, and the sixth fraction is partly sent to step F and partly to step C;

E. purifying the fifth fraction obtained in step D and which comprises prevalently isomers of dimethylnaphthalene, by cooling, subsequent washing, and crystallization in the presence of a low molecular weight alcohol selected from the group consisting of methanol, ethanol and propanol to obtain a first fraction consisting of 2,6 dimethylnaphthalene and a second fraction comprising prevalently isomers of dimethylnaphthalene, comprising the 2,6 dimethylnaphthalene isomer, wherein said second fraction obtained in the step E, comprising prevalently isomers of dimethylnaphthalene, comprising the 2,6 dimethylnaphthalene isomer, is partly sent to step C and partly to step F;

F. transalkylating the hydrocarbon mixture comprising naphthalene and/or isomers of dimethylnaphthalene and/or isomers of polymethylnaphthalene, in the presence of a solid acid catalyst and a mixture of methylated benzene solvents comprising benzene, toluene and xylenes, wherein an overall molar ratio between methyls and benzene ring of less than 2, to obtain a hydrocarbon mixture comprising a higher concentration of methylnaphthalene isomers and wherein said hydrocarbon mixture obtained is partly sent to step D by distillation and partly to step G, by distillation; and G. separating, by distillation, a mixture comprising benzene and mixtures of methylated benzene solvents, naphthalene and/or isomers of methylnaphthalene and/or isomers of dimethylnaphthalene and/or isomers of polymethylnaphthalene obtained in step F, to obtain a first fraction comprising a mixture of various methylated benzene solvents, naphthalene and methylnaphthalene isomers and a second fraction comprising dimethylnaphthalene isomers, including the 2,6 dimethylnaphthalene isomer, and polymethylnaphthalenes, wherein the first fraction is sent to step D and wherein all or part of the second fraction is sent step F.

23. The process according to claim 22, wherein in said separating the third fraction is sent to said alkylating, and in said transalkylating the hydrocarbon mixture comprises prevalently isomers of dimethylnaphthalene and/or isomers of polymethylnaphthalene.

24. The process according to claim 23, wherein in said transalkylating the hydrocarbon mixture comprises prevalently isomers of dimethylnaphthalene and isomers of polymethylnaphthalene.

25. The process according to claim 22, wherein said low molecular weight alcohol is methanol.

26. A process for the preparation of high purity 2,6-dimethylnaphthalene starting from hydrocarbon mixtures comprising naphthalene and/or isomers of methylnaphthalene and/or isomers of dimethylnaphthalene and/or isomers of polymethylnaphthalene, and from a methylating agent which are reacted in a benzene solvent in the presence of a catalyst comprising a zeolite, the process comprising:

A. enriching, by distillation, a hydrocarbon mixture comprising naphthalene and/or isomers of methylnaphthalene and/or isomers of dimethylnaphthalene and/or isomers of polymethylnaphthalene to obtain a first hydrocarbon fraction characterized by a higher concentration of said naphthalene compounds and a second fraction comprising prevalently of non-naphthalene compounds;

B. purifying the hydrocarbon mixture obtained in step A which comprises naphthalene and/or isomers of methylnaphthalene and/or isomers of dimethylnaphthalene and/or isomers of polymethylnaphthalene, by reacting said hydrocarbon mixture with a solid acid catalyst in the presence of a methylated benzene solvent, followed by separation into a first fraction consisting of a benzene solvent and said naphthalene compounds and into a second hydrocarbon fraction comprising prevalently heavy non-naphthalene compounds, initially present or formed during the purifying;

C. alkylating a hydrocarbon mixture comprising naphthalene and/or isomers of methylnaphthalene and/or isomers of dimethylnaphthalene and/or isomers of polymethylnaphthalene, to produce an effluent comprising a hydrocarbon mixture, enriched in a 2,6-dimethylnaphthalene isomer, wherein the alkylating is carried out in the presence of a methylating agent, a methylated benzene solvent, or mixtures of methylated benzene solvents, starting from toluene up to hexamethylbenzene, and a solid acid catalyst consisting of ZSM-12 zeolite and an inorganic ligand, said mixture of methylated benzene solvents have an overall molar ratio between methyls and aromatic benzene ring equal to or higher than 2;

D. separating, by distillation, a mixture containing an aqueous phase, benzene and mixtures of various methylated benzene solvents, naphthalene and/or isomers of methylnaphthalene and/or isomers of dimethylnaphthalene and/or isomers of polymethylnaphthalene obtained from step C and steps F and G, to obtain:

a first fraction prevalently comprising water and benzene, toluene and xylenes and characterized by an overall molar ratio between methyls and benzene ring of less than 2, a second fraction prevalently comprising tri-, tetra-, penta- and hexamethylbenzene and characterized by an overall molar ratio between methyls and benzene ring equal to or higher than 2 and preferably higher than 3, a third fraction prevalently comprising naphthalene, a fourth fraction prevalently comprising methylnaphthalene isomers, a fifth fraction prevalently comprising isomers of dimethylnaphthalene comprising the 2,6 dimethylnaphthalene isomer, and a sixth fraction prevalently comprising polymethylnaphthalenes, wherein the first fraction, after separating and removing the aqueous phase, by demixing, is partly sent to step B and partly to step F, the second fraction is partly sent to step B and partly to step C, the third fraction is partly sent to step F and partly to step C, the fourth fraction is sent to step C, the fifth fraction is sent to the subsequent step H, and the sixth fraction is partly sent to step F and partly to step C;

E. purifying first fraction from step H which prevalently comprises isomers of dimethylnaphthalene characterized by a high concentration of the 2,6 isomer and a low concentration of the 1,6 and 1,5 dimethylnaphthalene isomers, by cooling, subsequent washing and crystallization in the presence of a low molecular weight alcohol selected from methanol, ethanol and propanol to obtain a first fraction consisting of 2,6 dimethylnaphthalene and a second fraction prevalently comprising isomers of dimethylnaphthalene, comprising the 2,6 dimethylnaphthalene isomer, and where the second fraction is partly sent to step C and partly to step F;

F. transalkylating the hydrocarbon mixture comprising naphthalene and/or isomers of dimethylnaphthalene and/or isomers of polymethylnaphthalene, carried out in the presence of a solid acid catalyst and a mixture of methylated benzene solvents prevalently comprising benzene, toluene and xylenes and characterized by an overall molar ratio between methyls and benzene ring of less than 2, to obtain a hydrocarbon mixture characterized by a higher concentration of methylnaphthalene isomers and wherein said hydrocarbon mixture obtained in the present step F is sent to step G;

G. separating, by distillation, a mixture comprising benzene and mixtures of various methylated benzene solvents, naphthalene and/or isomers of methylnaphthalene and/or isomers of dimethylnaphthalene and/or isomers of polymethylnaphthalene obtained in step F, to obtain a first fraction consisting of a mixture of methylated benzene solvents, naphthalene and methylnaphthalene isomers and a second fraction prevalently consisting of dimethylnaphthalene isomers, including the 2,6 dimethylnaphthalene isomer, and polymethylnaphthalenes, wherein the first fraction is sent to step D and all or a part of the second fraction is sent to step F;

H. separating, by distillation, a hydrocarbon mixture prevalently comprising dimethylnaphthalene isomers to obtain a first fraction prevalently comprising dimethylnaphthalene isomers with a higher concentration of the 2,6 isomer and a lower concentration of 1,6 and 1,5 dimethylnaphthalene isomers, with respect to the initial concentrations of the mixture fed to the present step, and a second fraction prevalently comprising dimethylnaphthalene isomers with a lower concentration of the 2,6 isomer and higher concentration of 1,6 and 1,5 dimethylnaphthalene isomers, with respect to the initial concentrations of the mixture fed to the present step, wherein the first fraction obtained in the present step H is sent to step E and the second fraction is sent to step I; and I. isomerizating the hydrocarbon mixture consisting of the second fraction obtained in step H and prevalently containing dimethylnaphthalene isomers to obtain a hydrocarbon mixture characterized by a higher concentration of 2,6 dimethylnaphthalene isomer, with respect to the initial concentration of the mixture fed to the present step, wherein the isomerizating is carried out in the presence of a solid acid catalyst, and wherein the hydrocarbon mixture obtained in the present isomerizating step I is sent, either totally or partially, to step H.

27. The process according to claim 26, wherein in step D the third fraction is sent to step C, and in step F the hydrocarbon mixture comprises prevalently isomers of dimethylnaphthalene and/or isomers of polymethylnaphthalene. second fraction is sent to step I; and 28. The process according to claim 26, wherein said low molecular weight alcohol is methanol.

\* \* \* \* \*